(12) United States Patent
Carrick et al.

(10) Patent No.: US 7,739,054 B2
(45) Date of Patent: Jun. 15, 2010

(54) METHOD AND ALGORITHM FOR QUANTIFYING POLYNUCLEOTIDES

(75) Inventors: James M. Carrick, San Diego, CA (US); Jeffrey D. Chismar, San Diego, CA (US); Michael J. Gilly, San Diego, CA (US)

(73) Assignee: Gen-Probe Incorporated, San Diego, CA (US)

( * ) Notice: Subject to any disclaimer, the term of this patent is extended or adjusted under 35 U.S.C. 154(b) by 0 days.

(21) Appl. No.: 11/474,698

(22) Filed: Jun. 22, 2006

(65) Prior Publication Data

US 2006/0292619 A1    Dec. 28, 2006

Related U.S. Application Data

(60) Provisional application No. 60/693,455, filed on Jun. 22, 2005.

(51) Int. Cl.
  *G01N 33/50*   (2006.01)
  *C12Q 1/68*    (2006.01)
(52) U.S. Cl. ............................................. 702/19; 435/6
(58) Field of Classification Search ........................ None
  See application file for complete search history.

(56) References Cited

U.S. PATENT DOCUMENTS

| | | | |
|---|---|---|---|
| 6,066,458 A | 5/2000 | Haalnad et al. | |
| 6,303,305 B1 | 10/2001 | Wittwer et al. | |
| 6,387,621 B1 | 5/2002 | Wittwer | |
| 6,783,934 B1 | 8/2004 | McMillan et al. | |
| 6,911,327 B2 * | 6/2005 | McMillan et al. | 702/19 |
| 2003/0148302 A1 * | 8/2003 | Woo et al. | 435/6 |
| 2004/0096881 A1 | 5/2004 | McMillan et al. | |

FOREIGN PATENT DOCUMENTS

| | | |
|---|---|---|
| WO | 03/029924 A2 | 4/2003 |
| WO | 2005/030990 A1 | 4/2005 |

OTHER PUBLICATIONS

Purcell (Calculus with Analytical Geometry, Meridith Publishing Company, p. 112-113, 116-117 and 468-479, 1965).*
Heid et al. (Genome Research, vol. 6, p. 986-994, 1996).*
Weusten et al., "Principles of quantitation of viral loads using nucleic acid sequence-based amplification in . combination with homogeneous detection using molecular beacons", Nucl. Acids Res., 2002, 30(6):1-7, Oxford University Press, Great Britain.
Zhao et al., "Comprehensive Algorithm for Quantitative Real-Time Polymerase Chain Reaction," J. Comput. Biol., 2005, 12(8):1047-1064, Mary Ann Liebert, Inc., New York, NY.

* cited by examiner

*Primary Examiner*—Marjorie Moran
*Assistant Examiner*—Karlheinz R Skowronek
(74) *Attorney, Agent, or Firm*—Michael J. Gilly

(57) ABSTRACT

Machine executable method of analyzing growth curve data to identify the transition from a baseline phase into a growth phase. Applications of the method include analysis of results from time-dependent monitoring of amplicon synthesis in a nucleic acid amplification reaction to quantify a starting amount of a nucleic acid template in a test sample. The method advantageously simplifies the quantitation by circumventing the need to establish thresholds used for calculating initiation of the growth phase, to calculate derivatives, or to perform linear regression analysis.

16 Claims, 14 Drawing Sheets

METHOD AND ALGORITHM FOR QUANTIFYING POLYNUCLEOTIDES

RELATED APPLICATION

This application claims the benefit of U.S. Provisional Application No. 60/693,455, filed Jun. 22, 2005. The entire disclosure of this prior application is hereby incorporated by reference.

FIELD OF THE INVENTION

The present invention relates to the field of biotechnology. More specifically, the invention relates to polynucleotide quantitation using real-time nucleic acid amplification.

BACKGROUND OF THE INVENTION

The subfield of molecular diagnostics which relates to nucleic acid quantitation has embraced kinetic analysis as a means for interpreting results from nucleic acid amplification reactions. In these procedures, sometimes referred to as "real-time" amplification procedures, the amount of amplicon present in a nucleic acid amplification reaction mixture is monitored as a function of time. Ideally, the result of this monitoring is a growth curve having a sigmoid shape, where an initial baseline phase is followed by a growth phase, which is followed by a plateau phase.

Another important trend in the molecular diagnostics field is the drive toward full automation of laboratory procedures and analysis of results. Fully automated real-time nucleic acid assays require machine executable algorithms capable of analyzing data. In this regard, there is a requirement for data processing algorithms that accurately output an amount or concentration of a nucleic acid that gave rise to an observed amplification result.

Prior methods of automating the analysis of real-time amplification reactions have relied on mathematical treatments of growth curves. For example, certain algorithms are based on the slope of the log-linear segment of a growth curve, or on derivative-based analysis of most or all of the curve. Frequently, there is an additional requirement for calculating a "threshold" value which must be exceeded to indicate a true positive amplification result.

Unfortunately, the quantitative abilities of some prior methods for analyzing results from real-time nucleic acid amplification reactions are compromised at very low target levels (i.e., less than about 100 copies/reaction). This may be due to a fanning pattern which characterizes growth curves of reactions conducted using very low target levels, meaning that different reactions conducted using presumably identical initial target amounts produce amplicons at somewhat different rates. Stated differently, the kinetics of amplification in reactions conducted using very low template levels exhibit noticeable fluctuation, and this fluctuation leads to uncertainty in the final quantitative result generated by some algorithms. Methods that additionally require calculation of a threshold for indicating a positive result compound this uncertainty.

Thus, there exists a need for quantitative methods which are not severely compromised by problems related to fluctuation in data derived from real-time amplification of low levels of target.

SUMMARY OF THE INVENTION

A first aspect of the invention relates to a method for determining the amount of a nucleic acid in a test sample. In accordance with the method, first there is a step for amplifying a predetermined locus of the nucleic acid in an in vitro amplification reaction to create a nucleic acid amplification product. Next, there is a step for determining a value proportional to the amount of the nucleic acid amplification product present at different times during the in vitro amplification reaction, whereby there is created a collection of time-dependent values that collectively define a growth curve. Next, there is a step for performing a vector analysis on at least a portion of the growth curve to identify a time-dependent feature of the growth curve. This vector analysis includes steps for (a) establishing a plurality of pairs of first and second vectors at different points on the time dimension of the growth curve using the collection of time-dependent values, wherein each vector of a single pair of vectors among the plurality has the same origin, and wherein the head of the first vector and the head of the second vector of the single pair of vectors among the plurality are each positioned at different points on the growth curve. The next step in the vector analysis procedure involves identifying the time-dependent feature of the growth curve using the plurality of pairs of first and second vectors established in step (a) of the vector analysis. Finally, the invented method includes a step for determining from the time-dependent feature of the growth curve the amount of the nucleic acid in the test sample. In a preferred embodiment, step (b) of the vector analysis involves calculating for each different pair of vectors the value of a parameter that is dependent on that pair of vectors. For example, this parameter may be an angle between the vectors. When this is the case, step (b) of the vector analysis may further involve identifying a position on the growth curve at which the angle between vectors is a minimum angle. Alternatively, step (b) of the vector analysis may further involve identifying a position on the growth curve at which the angle between vectors is a maximum angle. In another preferred embodiment, each vector in a single pair of vectors has a different magnitude in the time dimension of the growth curve, these vectors being directionally similar vectors. In still another preferred embodiment, each vector in a single pair of vectors has a different magnitude in the time dimension of the growth curve, but are directionally opposed vectors. In yet another preferred embodiment, each vector in a single pair of vectors has the same magnitude in the time dimension of the growth curve, these vectors being directionally opposed vectors. In still yet another preferred embodiment, the invented method further includes a processing step before the step for performing the vector analysis. This processing step involves processing the collection of time-dependent values of the first determining step by a smoothing function to result in smoothed numerical data. When this is the case, the collection of time-dependent values used in step (a) of the vector analysis may be the smoothed numerical data resulting from this processing step. In a preferred embodiment of the method that includes the processing step, the smoothing function is either a moving average smoothing function, or a curve-fitting smoothing function. In another preferred embodiment of the method that includes the processing step, step (b) of the vector analysis involves calculating for each different pair of vectors the value of a parameter dependent on that pair of vectors. For example, this parameter may be an angle between the vectors. In another preferred embodiment of the method that includes the processing step, each vector in a single pair of vectors has a different magnitude in the time dimension of the growth curve, these vectors being directionally similar vectors. When this is the case, step (b) of the vector analysis may involve calculating for each pair of vectors the value of a parameter dependent on that pair of vectors. In a highly preferred embodiment, this parameter is an angle between the vectors. In another preferred embodiment of the method that includes the processing step, each vector in a single pair of vectors has a different magnitude in the time dimension of the growth curve, these vectors being directionally opposed vectors. When this is the case, step (b) of the vector analysis may involve calculating for each pair of vectors the value of a parameter dependent on that pair of vectors. For example, this parameter may be an angle between the vectors. In another preferred embodiment of the method that includes the processing step, each vector in a single pair of vectors has the same magnitude in the time dimension of the growth curve, these vectors being directionally opposed vectors. When this is the case, step (b) of the vector analysis may involve calculating for each pair of vectors the value of a parameter dependent on that pair of vectors. For example, this parameter may be an angle between the vectors. Generally speaking, the in vitro amplification reaction in the amplifying step of the invented method may be an isothermal in vitro amplification reaction. More preferably, the value proportional to the amount of the nucleic acid amplification product in the first determining step is a fluorescence value. Still more preferably, the step for determining from the time-dependent feature of the growth curve involves comparing the time-dependent feature of the growth curve with a standard calibration curve. Yet even more preferably, the step for performing the vector analysis is automated by a computer.

Another aspect of the invention relates to a method for quantifying an amount of a nucleic acid in a test sample. In accordance with the method, first there is a step for contacting the test sample with an amplifying agent. Next, there is a step for amplifying a predetermined locus of the nucleic acid in an in vitro amplification reaction to create a nucleic acid amplification product. Next, there is a step for determining a value proportional to the amount of the nucleic acid amplification product present at different times during the amplification reaction. Optionally, there is a step for processing the determined values using a smoothing function to result in processed values. Next, there is a step for performing a vector analysis on either (a) the determined values if the optional processing step is omitted or (b) the processed values if the optional processing step is included. The object of the vector analysis is to identify a time-dependent feature of the determined values or processed values. Finally, there is a step for calculating from the time-dependent feature the amount of the nucleic acid in the test sample.

Another aspect of the invention relates generally to a method of identifying a feature on a curve. In accordance with the method, first there is a step for obtaining numerical data for the curve. Next, there is a step for establishing a plurality of pairs of first and second vectors at different points on a first dimension of the curve using the numerical data. Each vector of a single pair of vectors among the plurality has the same origin, and the head of the first vector and the head of the second vector of the single pair of vectors among the plurality are each positioned at different points on the curve. Next, there is a step for identifying the feature on the curve using the plurality of pairs of first and second vectors from the establishing step. Generally speaking, the steps for establishing the plurality of vector pairs and identifying the curve feature are automated by a computer. In a preferred embodiment, the step for identifying the curve feature involves calculating for each pair of vectors among the plurality the value of a parameter dependent on that pair of vectors. For example, this parameter may be an angle between vectors. When this is the case, the identifying step may further involve identifying a position on the curve at which the angle between vectors is a minimum angle. Alternatively, the identifying step may further involve identifying a position on the curve at which the angle between vectors is a maximum angle. In another preferred embodiment, each vector in a single pair of vectors has a different magnitude in the first dimension of the curve, these vectors being directionally similar vectors. In still another preferred embodiment, each vector in a single pair of vectors has a different magnitude in the first dimension of the curve, these vectors being directionally opposed vectors. In yet another preferred embodiment, each vector in a single pair of vectors has the same magnitude in the first dimension of the curve, these vectors being directionally opposed vectors. In still yet another preferred embodiment, the invented method further includes a step for processing the numerical data from the obtaining step by a smoothing function to result in smoothed numerical data. When this is the case, the numerical data used in the step for establishing the plurality of pairs of vectors is the smoothed numerical data resulting from the processing step. In a preferred embodiment of the method that includes the processing step, the smoothing function in the processing step is either a moving average smoothing function, or a curve-fitting smoothing function. In a preferred embodiment of the method that includes the processing step, the identifying step involves calculating for each pair of vectors the value of a parameter dependent on that pair of vectors. For example, this parameter may be an angle between the vectors. In a preferred embodiment of the method that includes the processing step, each vector in a single pair of vectors has a different magnitude in the first dimension of the curve, these vectors being directionally similar vectors. When this is the case, the identifying step may involve calculating for each pair of vectors the value of a parameter dependent on that pair of vectors. For example, this parameter may be an angle between the vectors. In a preferred embodiment of the method that includes the processing step, each vector in a single pair of vectors has a different magnitude in the first dimension of the curve, these vectors being directionally opposed vectors. When this is the case, the identifying step may involve calculating for each pair of vectors among the plurality the value of a parameter dependent on that pair of vectors. For example, this parameter may be an angle between the vectors. In a preferred embodiment of the method that includes the processing step, each vector in a single pair of vectors has the same magnitude in the first dimension of the curve, these vectors being directionally opposed vectors. When this is the case, the identifying step may involve calculating for each pair of vectors among the plurality the value of a parameter dependent on that pair of vectors. For example, this parameter may be an angle between the vectors.

DEFINITIONS

The following terms have the following meanings for the purpose of this disclosure, unless expressly stated to the contrary herein.

As used herein, a "test sample" is any sample to be investigated for the presence of a particular polynucleotide species. Test samples include any tissue or polynucleotide-containing material obtained from a human, animal, environmental, laboratory-derived or synthetic sample.

As used herein, "polynucleotide" means either RNA, DNA, or a chimeric molecule containing both RNA and DNA.

An "analyte amplicon" is a polynucleotide product of an amplification reaction wherein an analyte polynucleotide served as the template for synthesis of polynucleotide copies or amplification products.

An "analyte polynucleotide" is a target polynucleotide that is to be replicated by a nucleic acid amplification reaction.

As used herein, a "detectable label" is a chemical species that can be detected or can lead to a detectable response. Detectable labels in accordance with the invention can be linked to polynucleotide probes either directly or indirectly, and include radioisotopes, enzymes, haptens, chromophores such as dyes or particles that impart a detectable color (e.g., latex beads or metal particles), luminescent compounds (e.g., bioluminescent, phosphorescent or chemiluminescent moieties) and fluorescent compounds. Fluorescent dyes that bind specifically to double-stranded DNA are still other examples of detection labels.

A "homogeneous assay" refers to a detection procedure that does not require physical separation of hybridized probe from non-hybridized probe prior to determining the extent of specific probe hybridization. Exemplary homogeneous assays, such as those described herein, can employ molecular beacons, molecular torches or other self-reporting probes which emit fluorescent signals when hybridized to an appropriate target, as well as other homogeneously detectable labels that will be familiar to those having an ordinary level of skill in the art.

As used herein, the terms "amplification" or "nucleic acid amplification" and variants thereof refer to in vitro procedures for obtaining multiple copies of a target nucleic acid sequence, its complement or fragments thereof. Generally speaking, amplification means increasing the number of these copies by at least 10 fold when compared with an initial amount present in a test sample.

As used herein, "thermal cycling" refers to repeated changes of temperature, (i.e., increases or decreases of temperature) in a reaction mixture. Samples undergoing thermal cycling may shift from one temperature to another, stabilize at that temperature, transition to a second temperature or return to the starting temperature. The temperature cycle may be repeated as many times as required to study or complete the particular chemical reaction of interest.

By "target nucleic acid" or "target" is meant a nucleic acid containing a target nucleic acid sequence. In general, a target nucleic acid sequence that is to be amplified will be positioned between two oppositely disposed oligonucleotides, and will include the portion of the target nucleic acid that is complementary to each of the oligonucleotides.

By "target nucleic acid sequence" or "target sequence" or "target region" is meant a specific deoxyribonucleotide or ribonucleotide sequence comprising all or part of the nucleotide sequence of a single-stranded nucleic acid molecule, and the deoxyribonucleotide or ribonucleotide sequence complementary thereto.

By "transcription associated amplification" is meant any type of nucleic acid amplification that uses an RNA polymerase to produce multiple RNA transcripts from a nucleic acid template. Conventionally, these amplification reactions employ at least one primer having a 3'-end that can be extended by the activity of a DNA polymerase. One example of a transcription associated amplification method, called "Transcription Mediated Amplification" (TMA), generally employs an RNA polymerase, a DNA polymerase, deoxyribonucleoside triphosphates, ribonucleoside triphosphates, and a promoter-template complementary oligonucleotide, and optionally may include one or more analogous oligonucleotides. Variations of TMA are well known in the art as disclosed in detail in Burg et al., U.S. Pat. No. 5,437,990; Kacian et al., U.S. Pat. Nos. 5,399,491 and 5,554,516; Kacian et al., PCT No. WO 93/22461; Gingeras et al., PCT No. WO 88/01302; Gingeras et al., PCT No. WO 88/10315; Malek et al., U.S. Pat. No. 5,130,238; Urdea et al., U.S. Pat. Nos. 4,868,105 and 5,124,246; McDonough et al., PCT No. WO 94/03472; and Ryder et al., PCT No. WO 95/03430. The methods of Kacian et al. are preferred for conducting nucleic acid amplification procedures of the type disclosed herein.

As used herein, an "oligonucleotide" or "oligomer" is a polymeric chain of at least two, generally between about five and about 100, chemical subunits, each subunit comprising a nucleotide base moiety, a sugar moiety, and a linking moiety that joins the subunits in a linear spacial configuration. Common nucleotide base moieties are guanine (G), adenine (A), cytosine (C), thymine (T) and uracil (U), although other rare or modified nucleotide bases able to hydrogen bond are well known to those skilled in the art. Oligonucleotides may optionally include analogs of any of the sugar moieties, the base moieties, and the backbone constituents. Preferred oligonucleotides of the present invention fall in a size range of about 10 to about 100 residues. Oligonucleotides may be purified from naturally occurring sources, but preferably are synthesized using any of a variety of well known enzymatic or chemical methods.

As used herein, a "probe" is an oligonucleotide that hybridizes specifically to a target sequence in a nucleic acid, preferably in an amplified nucleic acid, under conditions that promote hybridization, to form a detectable hybrid. A probe optionally may contain a detectable moiety which either may be attached to the end(s) of the probe or may be internal. Detection may either be direct (i.e., resulting from a probe hybridizing directly to the target sequence or amplified nucleic acid) or indirect (i.e., resulting from a probe hybridizing to an intermediate molecular structure that links the probe to the target sequence or amplified nucleic acid). The "target" of a probe generally refers to a sequence contained within an amplified nucleic acid sequence which hybridizes specifically to at least a portion of a probe oligonucleotide using standard hydrogen bonding (i.e., base pairing). A probe may comprise target-specific sequences and optionally other sequences that are non-complementary to the target sequence that is to be detected.

As used herein, an "amplification primer" is an oligonucleotide that hybridizes to a target nucleic acid, or its complement, and participates in a nucleic acid amplification reaction. For example, some amplification primers, or more simply "primers," may be optionally modified oligonucleotides which are capable of hybridizing to a template nucleic acid and which have a 3' end that can be extended by a DNA polymerase activity. In general, a primer will have a downstream target-complementary sequence, and optionally an upstream sequence that is not complementary to target nucleic acids. The optional upstream sequence may, for example, serve as an RNA polymerase promoter or contain restriction endonuclease cleavage sites.

As used herein, "time-dependent" monitoring of nucleic acid amplification, or monitoring of nucleic acid amplification in "real-time" refers to a process wherein an indicator of the amount of amplicon present in a nucleic acid amplification reaction is measured as a function of time and then used to determine a starting amount of template that was present in the reaction mixture at the time the amplification reaction was initiated. For example, the amount of amplicon can be measured prior to commencing each complete cycle of an amplification reaction that comprises thermal cycling, such as PCR. Alternatively, isothermal amplification reactions that do not require physical intervention to initiate the transitions between amplification cycles can be monitored continuously, or at regular time intervals (i.e., "read-cycles") to obtain information regarding the amount of amplicon present as a function of time.

As used herein, a "growth curve" refers to the characteristic pattern of appearance of a synthetic product, such as an amplicon, in a reaction as a function of time or cycle number. A growth curve is conveniently represented as a two-dimensional plot of time (x-axis) against some indicator of product amount, such as a fluorescence measurement (y-axis). Thus, growth curves conventionally have a time dimension represented on one axis. Some, but not all, growth curves have a sigmoid-shape.

As used herein, the "baseline phase" of a growth curve refers to the initial phase of the curve wherein the amount of product (such as an amplicon) increases at a substantially constant rate, this rate being less than the rate of increase characteristic of the growth phase (which may have a log-linear profile) of the growth curve. The baseline phase of a growth curve typically has a very shallow slope, frequently approximating zero.

As used herein, the "growth phase" of a growth curve refers to the portion of the curve wherein the measurable product substantially increases with time. Transition from the baseline phase into the growth phase in a typical nucleic acid amplification reaction is characterized by the appearance of amplicon at a rate that increases with time. Transition from the growth phase to the plateau phase of the growth curve begins at an inflection point where the rate of amplicon appearance begins to decrease.

As used herein, the "plateau phase" of a triphasic growth curve refers to the final phase of the curve. In the plateau phase, the rate of measurable product formation is substantially lower than the rate of amplicon production in the log-linear phase, and may even approach zero.

As used herein, a "vector" refers to a mathematical quantity which is described by both magnitude and direction. Vectors can be represented by use of a scaled vector diagram. On such a diagram, an arrow is drawn to represent the vector, with the vector having an obvious head and tail. The vector tail position is sometimes referred to as the "origin" of the vector. The magnitude of a vector is indicated by its length.

By "inflection" is meant a bending or curving.

By "inflection point" is meant a point on a curve at which there is a change in curvature from convex to concave or from concave to convex.

By "concave" is meant curved like the inside of a circle or sphere.

By "convex" is meant curved like the outside of a circle or sphere.

By "consisting essentially of" is meant that additional component(s), composition(s) or method step(s) that do not materially change the basic and novel characteristics of the present invention may be included in the present invention. Any component(s), composition(s), or method step(s) that have a material effect on the basic and novel characteristics of the present invention would fall outside of this term.

BRIEF DESCRIPTION OF THE DRAWINGS

FIG. 1A shows a biphasic growth curve having a baseline phase and a growth phase. FIG. 1B shows a triphasic growth curve having a baseline phase, a log-linear growth phase, and a plateau phase. Each distinct phase is separated from another by "transitions" which are illustrated by dotted circles. The transitions between the baseline phases and the growth phases exhibit concave curvature, and the transition between the growth phase and the plateau phase exhibits convex curvature. The maximum of the first derivative is indicated by "A" for each growth curve. The maximum of the second derivative is indicated by "B" for each growth curve.

DETAILED DESCRIPTION OF THE INVENTION

Introduction and Overview

Figure 1A:
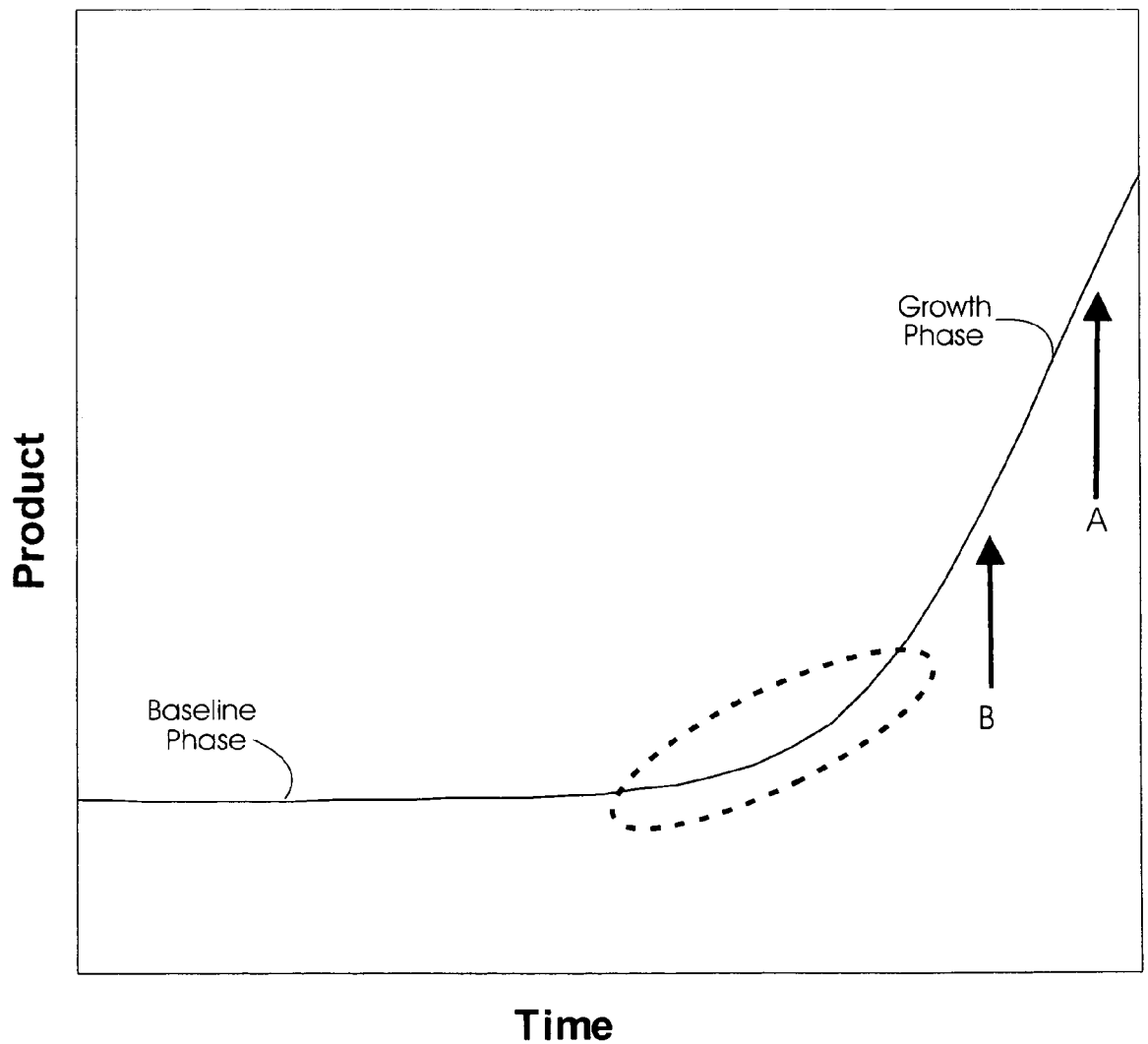
FIGS. 1A-1B illustrate actual growth curves.

Herein there are disclosed machine executable algorithms for analyzing curves represented by experimental data, such as that encountered in the time-dependent monitoring of nucleic acid amplification, or by mathematical functions. Rather than relying on analysis of the log-linear phase of a growth curve, or on identifying the time at which the amount of amplicon synthesized in the amplification reaction exceeds a threshold level, the invention employs a two-dimensional vector analysis to identify a feature corresponding to initiation of the upward concave curvature in a growth curve. Preferably, this identified feature is located between the baseline phase and the growth phase of the growth curve.

Testing of the vector-based analytical method showed that quantification of low levels of input target was superior when compared with an alternative algorithm based on linear regression analysis of the log-linear phase of the growth curve, and determination of the time at which the amplification signal exceeded a background threshold value. Such an alternative algorithm is described in the U.S. patent application having Ser. No. 60/659,874.

Still further, the disclosed analytical method advantageously eliminates the need for calculating derivatives or otherwise determining the slope of a portion of a growth curve, and further eliminates the need for establishing threshold values used for interpolating the amount of amplicon. Indeed, the disclosed methods and algorithms, which rely on the relationship between two vectors drawn on a curve, or on the data points representing a curve, exhibit excellent precision where different amplification chemistries may be involved such that non-ideal growth curves result.

Preferred Embodiments of the Invention

In preferred embodiments, the disclosed algorithms are used for analyzing results obtained from time-dependent monitoring of amplicon synthesis in a nucleic acid amplification reaction. As commonly practiced, a detectable signal indicating the quantity of an analyte amplicon synthesized in a nucleic acid amplification reaction is monitored at different times during the course of the reaction. Amplification is generally effected by the activity of oligonucleotides that have defined sequences, and that amplify a predetermined locus of the nucleic acid target. The detectable signal may be, for example, a fluorescent signal, an electronic signal, an electrochemical or electrochemiluminescent signal. The detectable signal may be monitored at regular cycle intervals, or at regular or continuous time intervals.

Simply stated, the disclosed algorithms involve performing a vector analysis of the data to be analyzed in order to identify a feature on a growth curve. Using this approach, which preferably involves identifying at least one feature (such as an angle) which characterizes the relationship between two vectors established using the experimental data, there is eliminated any need for employing a threshold to indicate initiation of a growth phase. In a preferred embodiment, the disclosed method involves performing a vector analysis on at least a portion of a growth curve representing time-dependent readings of amplicon synthesis. The vector analysis involves establishing a plurality of pairs of vectors at different points on the time axis of the growth curve. Each vector in a single pair shares the same origin, and the heads of the two vectors in the pair are positioned at different points on the growth curve (see FIGS. 5A and 5B). The time-dependent feature of the growth curve can be identified using the plurality of pairs of first and second vectors established in this manner. In certain embodiments, prior to performing the vector analysis there is an optional step for curve-fitting or "smoothing" of values representing amplicon synthesis in the growth curve. In this instance the vector analysis preferably carried out using the smoothed or "fitted" curve instead of raw data. The products of these steps can easily be used for creating standard curves, or for determining a feature of a growth curve representing an amplification reaction conducted using a test sample. In this way, the starting amount of polynucleotide present in the test sample can be quantified.

Useful Amplification Methods

Examples of amplification methods useful in connection with the present invention include: Transcription Mediated Amplification (TMA), Nucleic Acid Sequence-Based Amplification (NASBA), the Polymerase Chain Reaction (PCR), Strand Displacement Amplification (SDA), Self-Sustained Sequence Replication (3SR), DNA Ligase Chain Reaction (LCR) and amplification methods using self-replicating polynucleotide molecules and replication enzymes such as MDV-1 RNA and Q-beta enzyme. Methods for carrying out these various amplification techniques respectively can be found in U.S. Pat. No. 5,399,491, published European patent application EP 0 525 882, U.S. Pat. No. 4,965,188, U.S. Pat. No. 5,455,166, Guatelli et al., *Proc. Natl. Acad. Sci. USA* 87:1874-1878 (1990), International Publication No. WO 89/09835, U.S. Pat. No. 5,472,840 and Lizardi et al., *Trends Biotechnol.* 9:53-58 (1991). The disclosures of these documents which describe how to perform nucleic acid amplification reactions are hereby incorporated by reference.

Of course, other methods of amplifying nucleic acids can also be analyzed using the algorithms and methods disclosed herein. Indeed, certain preferred embodiments employ time-dependent monitoring of amplification reactions that require only a single extendable primer, and particularly include transcription-associated amplification systems that employ a single extendable primer in combination with a 3'-blocked oligonucleotide. Exemplary nucleic acid amplification methods based on the use of a single extendable primer are presented in U.S. patent application Ser. No. 11/213,519, filed Aug. 26, 2005 and published Mar. 2, 2006. The disclosure of this application is incorporated by reference herein.

In another preferred embodiment of the invention, nucleic acid sequences are amplified using a TMA protocol. According to this protocol, the reverse transcriptase which provides the DNA polymerase activity also possesses an endogenous RNase H activity. One of the primers used in this procedure contains a promoter sequence positioned upstream of a sequence that is complementary to one strand of a target nucleic acid that is to be amplified. In the first step of the amplification, a promoter-primer hybridizes to the target RNA at a defined site. Reverse transcriptase creates a complementary DNA copy of the target RNA by extension from the 3' end of the promoter-primer. Following interaction of an opposite strand primer with the newly synthesized DNA strand, a second strand of DNA is synthesized from the end of the primer by reverse transcriptase, thereby creating a double-stranded DNA molecule. RNA polymerase recognizes the promoter sequence in this double-stranded DNA template and initiates transcription. Each of the newly synthesized RNA amplicons re-enters the TMA process and serves as a template for a new round of replication, thereby leading to an exponential expansion of the RNA amplicon. Since each of the DNA templates can make 100-1000 copies of RNA amplicon, this expansion can result in the production of 10 billion amplicons in less than one hour. The entire process is autocatalytic and is performed at a constant temperature.

Useful Probe Labeling Systems and Detectable Moieties

Preferred detectable labels for probes in accordance with the present invention are detectable in homogeneous assay systems (i.e., where, in a mixture, bound labeled probe exhibits a detectable change, such as stability or differential degradation, compared to unbound labeled probe).

Essentially any labeling and detection system that can be used for monitoring specific nucleic acid hybridization can be used in conjunction with the present invention. Included among the collection of useful labels are fluorescent moieties (either alone or in combination with "quencher" moieties), chemiluminescent molecules, and redox-active moieties that are amenable to electronic detection methods. In some embodiments, preferred fluorescent labels include non-covalently binding labels (e.g., intercalating dyes) such as ethidium bromide, propidium bromide, chromomycin, acridine orange, and the like. In other embodiments, the use of covalently bound fluorescent agents is preferred. Preferred chemiluminescent molecules include acridinium esters. Examples of these detectable labels have been disclosed by Arnold et al., in U.S. Pat. No. 5,283,174 for use in connection with homogenous protection assays. Preferred electronic labeling and detection approaches are disclosed in U.S. Pat. Nos. 5,591,578 and 5,770,369, and the published international patent application WO 98/57158. Redox active moieties useful as labels in the present invention include transition metals such as Cd, Mg, Cu, Co, Pd, Zn, Fe and Ru.

In some applications, probes exhibiting at least some degree of self-complementarity are desirable to facilitate detection of probe:target duplexes in a test sample without first requiring the removal of unhybridized probe prior to detection. By way of example, structures referred to as "molecular torches" and "molecular beacons" are designed to include distinct regions of self-complementarity and regions of target-complementarity. Molecular torches are fully described in U.S. Pat. No. 6,361,945, and molecular beacons are fully described in U.S. Pat. No. 5,925,517, the disclosure of these patents being incorporated by reference herein. Both of these self-reporting probes include a label pair that interacts when the probe is in a closed conformation in the absence of any hybridized target. Hybridization of the target nucleic acid and the target complementary sequence separates the self-complementary portions of the probes, thereby shifting the probes to an open conformation. The shift to the open conformation is detectable due to reduced interaction of the label pair, which may be, for example, a fluorophore and a quencher (e.g., DABCYL and EDANS).

Molecular torches, molecular beacons and the like preferably are individually labeled with an interactive pair of detectable labels. Examples of detectable labels that are preferred as members of an interactive pair of labels interact with each other by FRET or non-FRET energy transfer mechanisms. Fluorescence resonance energy transfer (FRET) involves the radiationless transmission of energy quanta from the site of absorption to the site of its utilization in the molecule, or system of molecules, by resonance interaction between chromophores, over distances considerably greater than interatomic distances, without conversion to thermal energy, and without the donor and acceptor coming into kinetic collision. The "donor" is the moiety that initially absorbs the energy, and the "acceptor" is the moiety to which the energy is subsequently transferred. In addition to FRET, there are at least three other "non-FRET" energy transfer processes by which excitation energy can be transferred from a donor to an acceptor molecule.

Examples of donor/acceptor label pairs that may be used in connection with the invention, making no attempt to distinguish FRET from non-FRET pairs, include fluorescein/tetramethylrhodamine, IAEDANS/fluororescein, EDANS/DABCYL, coumarin/DABCYL, fluorescein/fluorescein, BODIPY FL/BODIPY FL, fluorescein/DABCYL, lucifer yellow/DABCYL, BODIPY/DABCYL, eosine/DABCYL, erythrosine/DABCYL, tetramethylrhodamine/DABCYL, Texas Red/DABCYL, CY5/BH1, CY5/BH2, CY3/BH1, CY3/BH2 and fluorescein/QSY7 dye. Those having an ordinary level of skill in the art will understand that when donor and acceptor dyes are different, energy transfer can be detected by the appearance of sensitized fluorescence of the acceptor or by quenching of donor fluorescence. When the donor and acceptor species are the same, energy can be detected by the resulting fluorescence depolarization. Non-fluorescent acceptors such as DABCYL and the QSY 7 dyes advantageously eliminate the potential problem of background fluorescence resulting from direct (i.e., non-sensitized) acceptor excitation. Preferred fluorophore moieties that can be used as one member of a donor-acceptor pair include fluorescein, ROX, TAMARA, and the CY dyes (such as CY5). Highly preferred quencher moieties that can be used as another member of a donor-acceptor pair include DABCYL and the BLACK HOLE QUENCHER moieties which are available from Biosearch Technologies, Inc., (Novato, Calif.).

Certain amplicon monitoring procedures most commonly used in connection with PCR-based methods rely on the use of DNA binding dyes or probes which can be digested by a nuclease activity. In the first instance, the amount of analyte amplicon present in a reaction preferably is monitored using fluorescent double-stranded DNA recognizing compounds. This is possible because the amount of double-stranded amplification product usually exceeds the amount of nucleic acid originally present in the sample to be analyzed. Double-stranded DNA specific dyes may be used in these monitoring procedures so that, upon excitation with an appropriate wavelength of light, enhanced fluorescence results only if the dye is bound to double-stranded DNA. Preferably, only those dyes are used which, like SYBR Green I (Molecular Probes/Invitrogen Corporation; CA), do not affect the efficiency of the PCR reaction. In an alternative procedure, the amplification product is detected using a single-stranded hybridization probe which is labeled with a fluorescent entity. The fluorescence emission of this entity is quenched by a second label which is present on the same probe, and which acts as a quenching compound. During the annealing step of the PCR reaction, the probe hybridizes to its target sequence, and, subsequently, during the extension of the primer, the DNA polymerase having a 5'-3'-exonuclease activity digests the hybridization probe such that the fluorescent entity is separated from the quencher compound. After appropriate excitation, fluorescence emission can be monitored as an indicator of accumulating amplification product.

Synthetic techniques and methods of bonding labels to nucleic acids and detecting labels are well known in the art (e.g., see Sambrook et al., *Molecular Cloning, A Laboratory Manual*, 2nd ed. (Cold Spring Harbor Laboratory Press, Cold Spring Harbor, N.Y., 1989), Chapter 10; Nelson et al., U.S. Pat. No. 5,658,737; Woodhead et al., U.S. Pat. No. 5,656,207; Hogan et al., U.S. Pat. No. 5,547,842; Arnold et al., U.S. Pat. No. 5,283,174; Kourilsky et al., U.S. Pat. No. 4,581,333), and Becker et al., European Patent App. No. 0 747 706.

Development of Vector-Based Approaches for Complex Curve Analysis

Our experience with real-time nucleic acid amplification indicated that curve shapes differed substantially when reactions were initiated using high and very low levels of analyte polynucleotide. More specifically, reactions conducted using high levels of analyte polynucleotide yielded curves having generally sigmoid shapes. Conversely, reactions conducted using very low levels of analyte polynucleotide yielded biphasic curves having a baseline that transitioned into a growth phase, wherein the signal indicating amplicon accumulation increased continuously throughout the monitoring period. We further observed that reactions conducted using very low levels of analyte polynucleotide frequently exhibited a "fanning" pattern wherein parallel reactions conducted using the same low target levels displayed growth curves with a range of slopes. An example of nucleic acid amplification reactions that were monitored as a function of time, and that yielded growth curves exhibiting "fanning" patterns, can be seen in FIG. 13. Methods for analyzing growth curves using derivative-based calculations are frequently challenged when presented with results that exhibit fanning.

Despite possible differences in curve shapes, we discovered that essentially all growth curves arising from reactions initiated using any particular level of analyte polynucleotide substantially shared a common time at which the amplicon signal emerged from a baseline phase. Stated differently, the curves characteristic of amplification reactions initiated with a single high level of analyte polynucleotide shared a common time of emergence (i.e., the end of the baseline phase). Similarly, the curves characteristic of amplification reactions initiated with a single low level of analyte polynucleotide shared a common time of emergence from the baseline phase, even when the different reactions showed evidence of fanning.

Accordingly, it was of interest to develop a mathematical approach for accurately determining the time at which any particular amplification reaction transitioned from a baseline phase to a growth phase. Such an approach would facilitate identification of a common feature of all growth curves, and would not require that different curves in the analysis share similar shapes.

Figure 6:
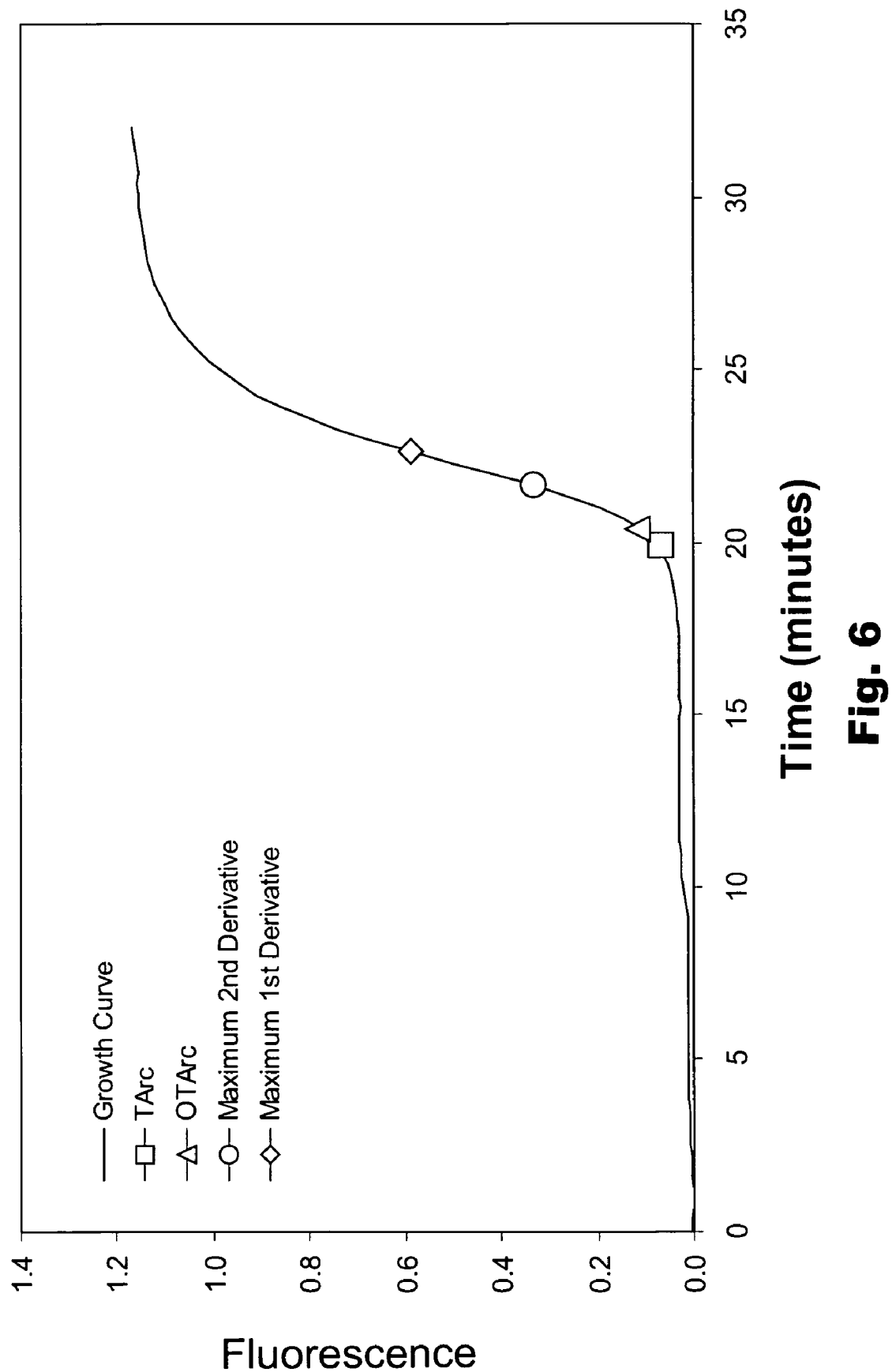
FIG. 6 shows a growth curve representing actual results obtained in a nucleic acid amplification reaction. The growth curve presents raw experimental results that did not include smoothing. Superimposed on the growth curve are indicators showing the positions for TArc, OTArc, the maximum of the second derivative, and the maximum of the first derivative.
Figure 13:
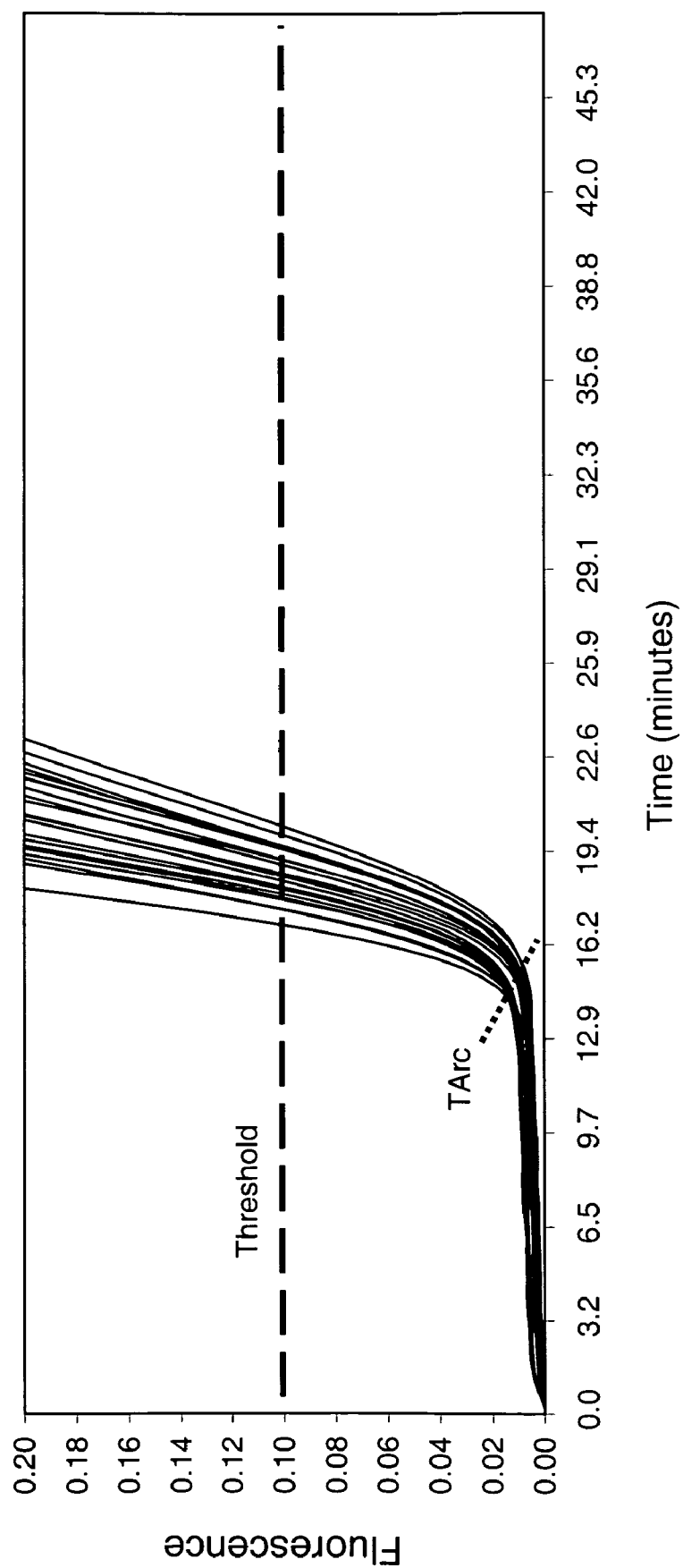
FIG. 13 shows a series of growth curves representing the amount of nucleic acid amplification product (measured by fluorescence signal) synthesized as a function of time for nucleic acid amplification reactions conducted using 5,000 copies/reaction of an analyte polynucleotide. The horizontal, heavy dashed line arbitrarily set at 0.10 fluorescence units indicates points on the growth curves that would be identified using a threshold-based algorithm to indicate the time at which a fluorescent signal was scored as positive. The inclined dotted line indicates points on the growth curves that would be identified using the vector-based algorithm for identifying TArc values.

Positive attributes of the vector-based curve analysis methods disclosed herein can be appreciated from FIG. 13, which shows how the influence of the fanning effect is reduced when compared with threshold-based methods of curve analysis. More particularly, the figure shows how the TArc values (indicated by the inclined dotted line) vary over a narrow range compared with the time values determined when fanned growth curves are required to exceed a threshold (indicated by the heavy dashed line). Moreover, it should be apparent that derivative-based curve analysis methods (e.g., based on identifying the maximum of a first or a second derivative) also would identify points on fanned growth curves that would have reduced precision. Notably, the relative positions of these different features of an example growth curve are illustrated in FIG. 6. Thus, the vector-based methods disclosed herein advantageously yield more precise results when compared with either threshold-based curve analysis methods, or derivative-based curve analysis methods.

Application of the Vector-Based Analysis

Figure 1B:
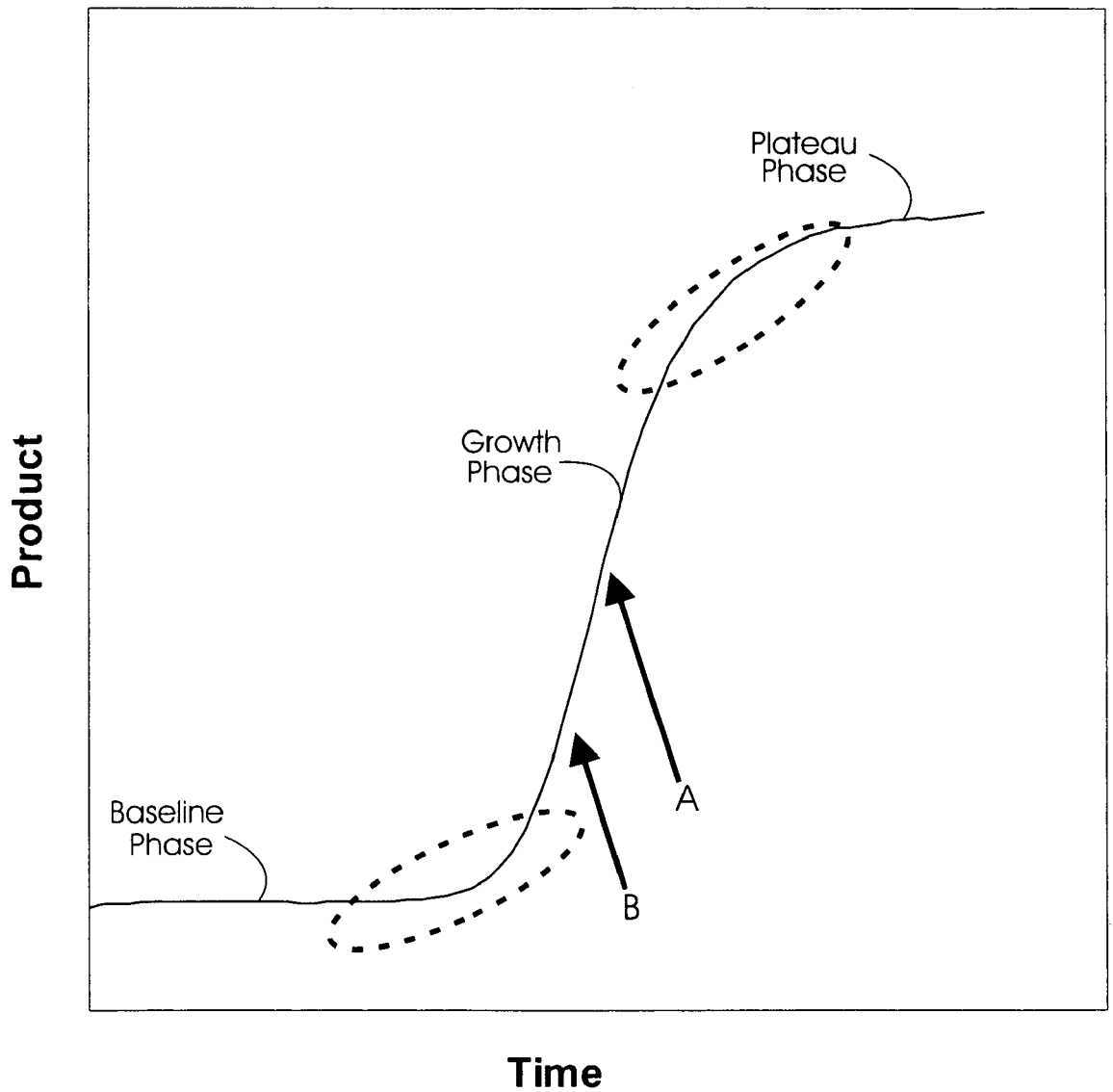

Generally speaking, the vector-based methods and algorithms disclosed herein can be applied to the analysis of any curve. However, the methods are preferably applied to the analysis of "growth curves" that include a baseline phase and a growth phase. FIG. 1A illustrates a biphasic growth curve that essentially consists of an early baseline phase and a later growth phase. The growth phase of the curve is characterized by a positive slope, meaning that the y-component of the curve increases as a function of time. Significantly, the slope of the growth phase portion of the curve is greater than the slope of the baseline phase. FIG. 1B illustrates a triphasic growth curve that further includes a plateau phase. The slope of the curve within the region of the plateau phase is less than that of the growth phase. To simplify terminology, the growth phase of a triphasic growth curve is alternatively referred to herein as the "growth phase" or "log-linear" phase. The log-linear phase conventionally includes the portion of the growth curve wherein amplicon production is exponential. In certain respects, the curve illustrated in FIG. 1A can be considered a truncated version of the curve illustrated in FIG. 1B. Truncation of a curve may be mediated by including or otherwise allowing only for analysis of the portion of the curve having a y-axis value less than a specified amount or percentage of the maximum measured value.

Each of the curves illustrated in FIGS. 1A-1B includes a transition between the different phases (indicated by dotted circles). These transitions mark brief periods during which the curves cannot be considered to be only in one of the three idealized phases (baseline, growth/log-linear, or plateau). Identifying the positions of the transition phases of growth curves frequently provides valuable information, and is one object of the invention. More particularly, it was of interest to identify the conclusion of the baseline phase, and the start of the transition into the growth phase or log-linear phase of a curve.

One aspect of the disclosed method and algorithm relates to performing a vector analysis on data that characterizes a measurable result as a function of time. In this regard, the quantitative method preferably involves a vector analysis for identifying a feature of a growth curve which indicates a transition from the baseline phase into the growth phase of a curve. Because there are alternative parameters that can be determined in the analysis, the general term "feature" is applied with the intention of capturing the various alternatives without limitation. Examples of these different parameters include: (1) the angle between two vectors drawn on a growth curve representing experimental data, (2) the rate of change of the angle between two vectors as a function of the time component of a growth curve representing experimental data, and (3) the magnitude of a third vector which joins the arrowheads of two vectors drawn on a growth curve representing experimental data.

In certain embodiments of the vector analysis, the feature identified for each growth curve relates to the angle between paired sets of vectors drawn on the curve as described herein. In one embodiment, the identified feature is the position along the time axis of the curve which is associated with the maximum angle between the paired sets of vectors (i.e., "TArc" herein). In a different embodiment, the identified feature is the position along the time axis of the curve which is associated with the minimum angle between the paired sets of vectors (i.e., "OTArc" herein).

Vector Analysis

The present invention employs a vector analysis to determine the point at which a growth curve begins to curve or "inflect" upward. This determined point, which may be the "TArc" or the "OTArc," can be used to create a calibration curve, or to establish a parameter of an amplification reaction that relates to the amount or concentration of an analyte polynucleotide in a test sample. This may involve comparing the determined time-dependent feature of the growth curve (i.e., the TArc or OTArc) obtained for a test sample with a standard calibration curve. The vector analysis is most conveniently carried out using growth curves having data points distributed over substantially uniform time intervals. The essential concept underlying the vector analysis is illustrated in FIGS. 2-3, and FIG. 5.

Algorithm Employing Directionally Similar Vectors—TArc

In one embodiment, the vector-based analytical method employs vectors that are directionally similar. This means that the vectors share the same direction in their x-components. Thus, for example, vectors that are directionally similar will have x-components directed toward increasing x-values. This is distinguished from the situation characterizing directionally opposed vectors, wherein one vector is directed opposite the other in the x-component.

Figure 2:
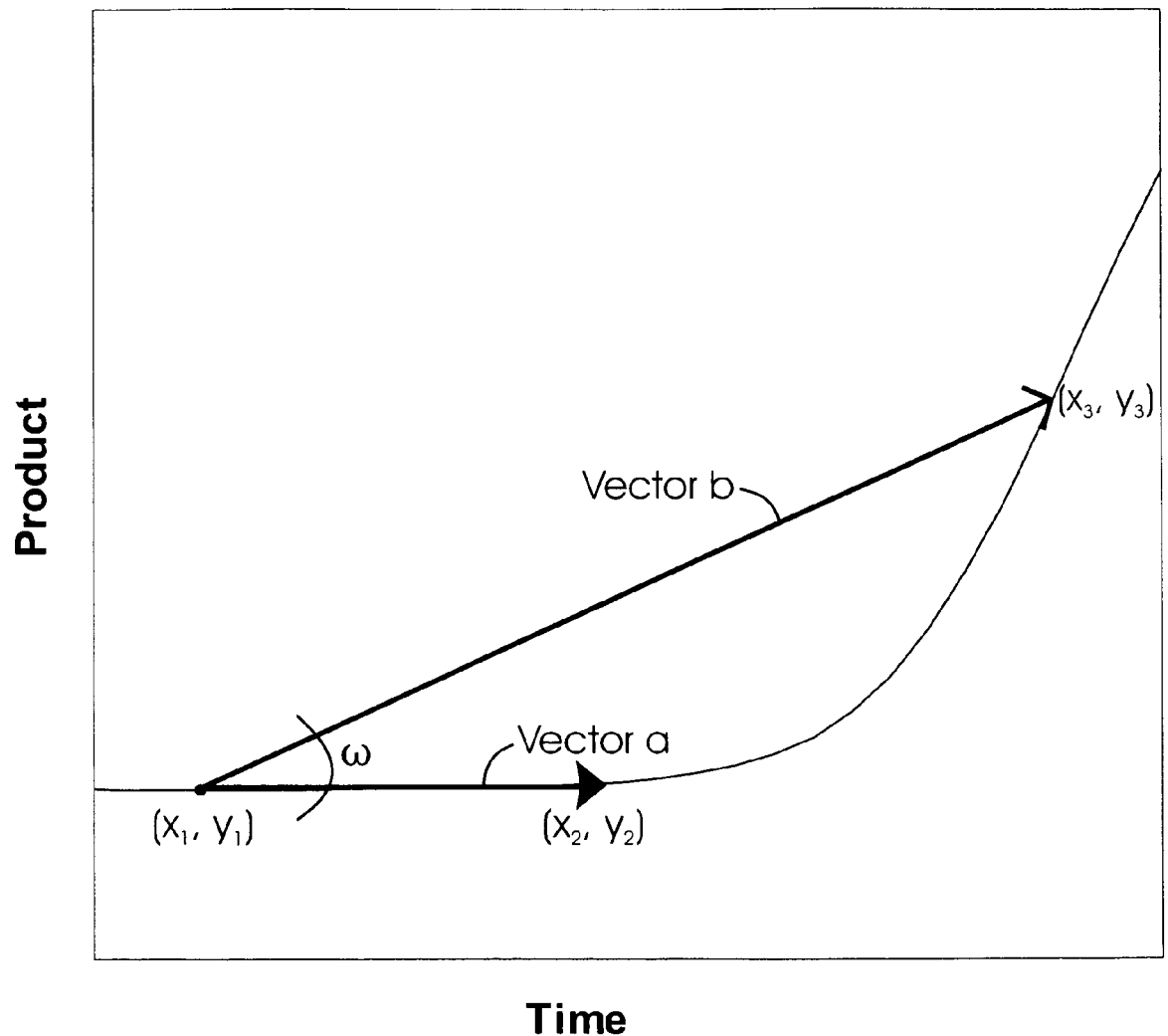
FIG. 2 illustrates a paired set of two vectors (vectors "a" and "b") drawn on a portion of a growth curve. The angle between the two vectors is identified as $\omega$.
Figure 3:
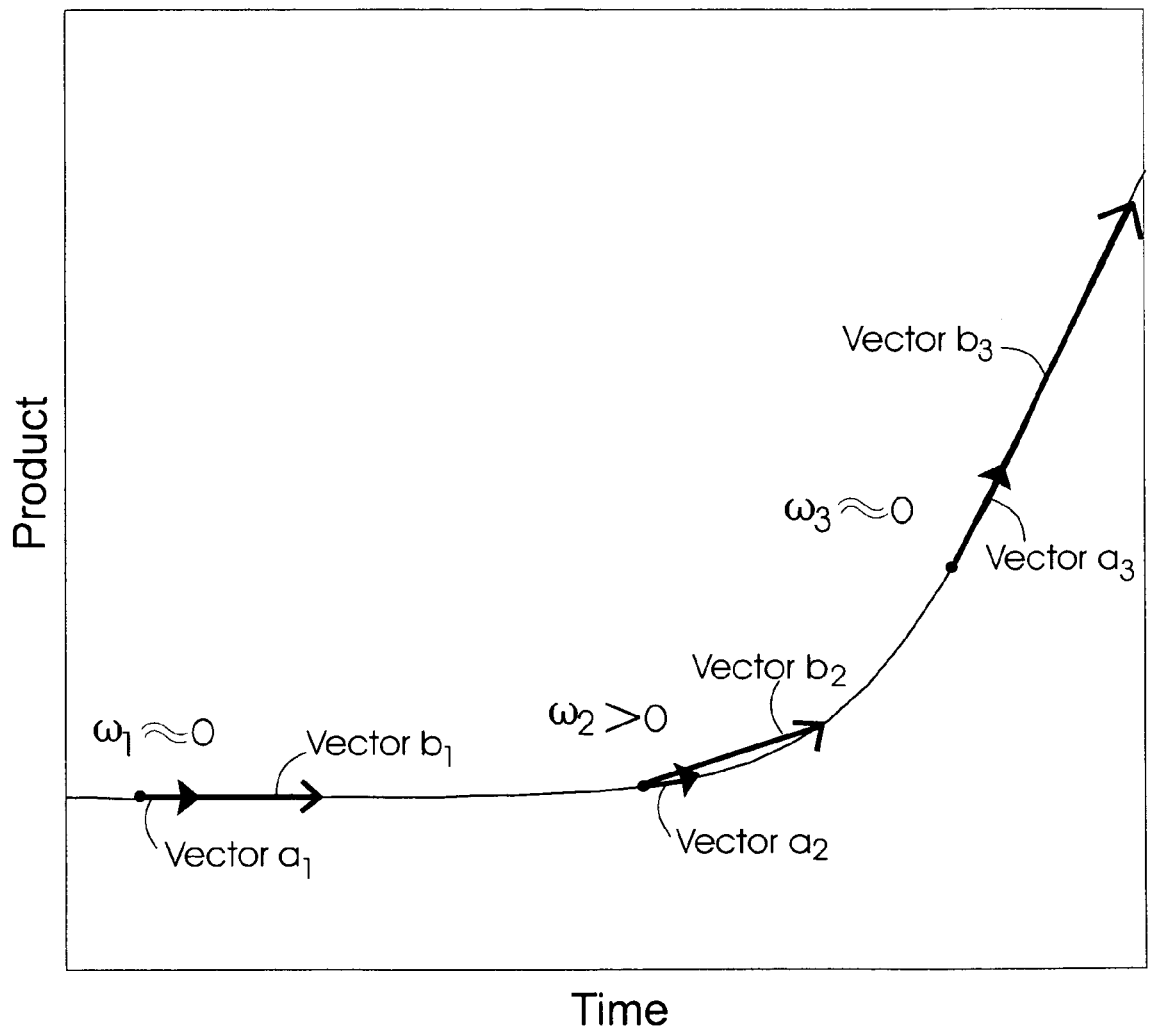
FIG. 3 illustrates a portion of a growth curve with three paired sets of vectors superimposed thereon at different positions. Each vector pair (i.e., vector a and vector b) is identified by a numerical subscript. The middle pair of vectors is shown as defining an angle ($\omega$) that is greater than the angle between the other vector pairs.

FIG. 2 illustrates the arrangement of a single paired set of directionally similar vectors drawn on an example growth curve. As indicated in the figure, a first vector (i.e., vector a) is established having its origin (i.e., tail terminus) positioned on a first data point (x1,y1) of the growth curve, and its head positioned on a second data point (x2,y2) of the same growth curve. The x-component (i.e., the time or cycle number axis) of the second data point has a value greater than the x-component of the first data point (i.e., x2>x1). For the purpose of illustration, if the growth curve is parsed into 5 second intervals in the time dimension, then the time value of the first data point can be 0 seconds and the time value of the second data point can be 5 seconds. In this illustration the time values of the two data points would be spaced apart by one unit (i.e., 5 seconds) in the time dimension of the growth curve. The magnitude of the first vector would simply be the distance separating the first and second data points. The y-components of the first and second data points correspond to the magnitudes of the amplicon signals measured at the specified time points. A second vector (vector b) is established having its origin positioned on the same first data point (x1,y1) of the growth curve that was used for the first vector, and its head positioned on a third data point (x3,y3) of the growth curve having an x-component greater than the x-component of the second data point of the first vector (i.e., x3>x2). For example, if the time dimension values of the two data points used to establish the first vector are separated by one unit on the x-axis, then the two data points used to establish the second vector should be separated on the x-axis by an amount greater than this number.

Preferably, the magnitude of the x-component of the second vector is greater than the magnitude of the x-component of the first vector, more preferably by at least 2 fold, still more preferably by at least 5 fold, still yet more preferably by at least 10 fold, and even still yet more preferably by at least 20 fold. In some highly preferred embodiments, the x-component of the second vector is greater than the x-component of the first vector by 25 fold or less, more preferably by 20 fold or less, or even by 15 fold or less. In certain highly preferred embodiments, the x-component of the second vector is greater than the x-component of the first vector by 2-25 fold, more preferably by 5-25 fold, more preferably by 10-20 fold, or still more preferably by 15-20 fold. For example, the x-component of the second vector may be greater than the x-component of the first vector by 17 fold. In this latter instance, if one unit in the time dimension of the growth curve equals 5 seconds, then the x-component of the second vector would be 85 seconds. It should be apparent that the y-component of the third data point corresponds to the magnitude of the amplicon signal measured at the specified time point.

In accordance with the invention, paired sets of two vectors (i.e., vector a and vector b), are established at regular time intervals, or cycle number intervals, along the growth curve, with each vector of a single set of paired vectors sharing a common origin (i.e., the data point corresponding to the tail of each vector). The magnitudes of the x-components of the first and second vectors in each paired set of vectors are held constant for the analysis. For example, if the magnitude of the x-component of the first vector in each pair is 5 seconds, then the magnitude of the x-component of the second vector in each pair can be held constant at, for example, 85 seconds. This results in a plurality of paired sets of two vectors, with the origins of the different paired sets of vectors being positioned at different time points. Table 1 illustrates how the x-component of paired sets of directionally similar vectors would increment in a reiterative process of establishing paired sets of vectors, with "x1" being the value of the x-coordinate of the shared origin, "x2" being the value of the x-coordinate at the head of the first vector, and "x3" being the value of the x-coordinate at the head of the second vector. FIG. 3 illustrates the positioning of three sets of vector pairs. Preferably, a plurality of the regularly spaced time points along the growth curve serve as the origins of different paired set of vectors.

TABLE 1

Incrementing the X-Component of Directionally Similar Vector Sets

| Increment No. | X1 (sec) | X2 (sec) | X3 (sec) |
|---|---|---|---|
| 1 | 0 | 5 | 85 |
| 2 | 5 | 10 | 90 |
| 3 | 10 | 15 | 95 |
| 4 | 15 | 20 | 100 |
| 5 | 20 | 25 | 105 |
| N | n | n + 5 | n + 85 |

Once the paired sets of vectors are established, at least one feature characterizing the relationship between two vectors of a single set is then identified or determined. In a preferred embodiment, the angle (ω) between the two vectors is determined using standard mathematical techniques that will be familiar to those having an ordinary level of skill in the art. The determined angle is associated with a time, or cycle number value along the growth curve. For example, the angle between two vectors (i.e., vector a and vector b) can be determined according to equation (1).

$$\omega = \arccos[a \cdot b/(\|a\|\|b\|)] \quad (1)$$

Figure 4A:
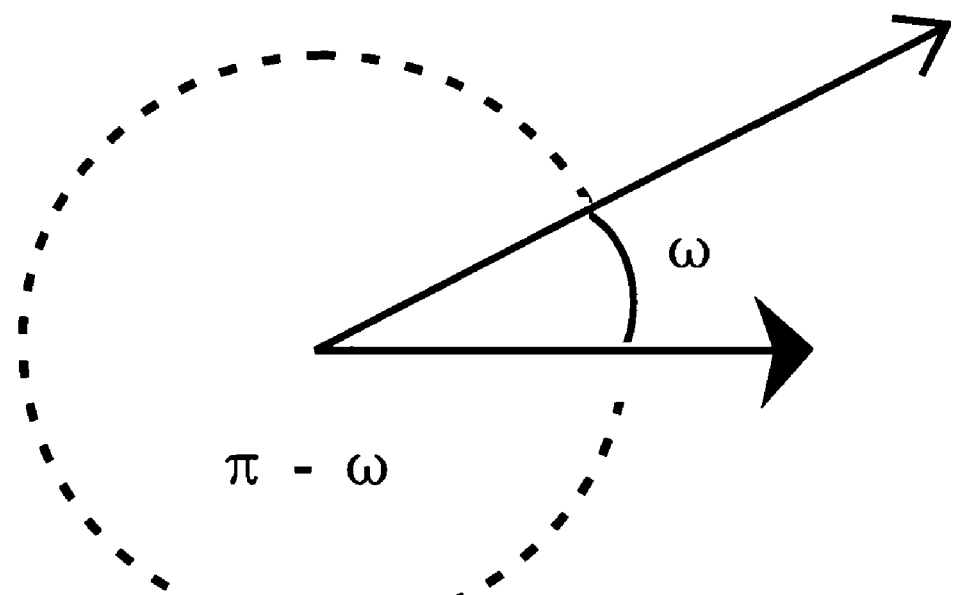
FIGS. 4A-4B illustrates the relationship between calculated values for angle $\omega$ and the remaining portion of a circle. Panel A illustrates two vectors that are directionally similar. Panel B illustrates two vectors that are directionally opposed.
Figure 4B:
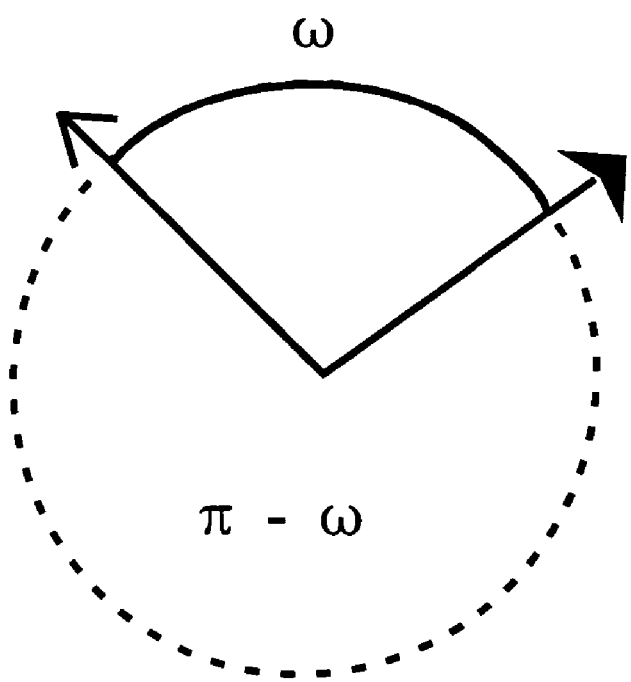

Those having an ordinary level of skill in the art will understand from equation (1) that the dot product of two vectors has the property defined by equation (2), where angle omega (ω) is the angle between vector a and vector b (assuming that the two vectors are non-zero, so the angle between them is well defined). The angle between the vectors has a numerical value in the interval (0, π). For clarity, FIG. 4 illustrates the relationship between the calculated values of angle omega (ω) and the remaining portion of a circle. Since the dot product and the norms of the vectors are easily computed, one can use this formula to calculate the angle between the vectors.

$$a \cdot b = \|a\|\|b\|\cos(\omega) \quad (2)$$

Thus, each time value along the x-axis of the growth curve can be associated with an angle value. This conveniently can be accomplished using a tabular format.

The angle (ω) between the two vectors will reach a maximum value within the time interval encompassing the upward concave inflection of the growth curve, and that point on the time axis is said to be the "TArc." Because the two vectors will be separated by substantial angles at the initiation and conclusion of the growth phase or log-linear phase of the growth curve, and because the time values corresponding to the first instance are of greatest interest, it is convenient, but not required to perform the vector analysis on the portion of the growth curve that precedes the conclusion of the growth phase of the growth curve. This can be accomplished, for example by using a sliding window vector analysis that excludes the portion of the curve characterized by convex curvature and the plateau phase. In some instances, this may involve analyzing the portion of the growth curve that represents a fixed percentage, such as 75% or 85%, of the maximum signal for amplicon production. By "sliding window" vector analysis, is meant a reiterative process of establishing vectors and determining the angle therebetween, and then incrementing along the x-axis of the growth curve to repeat the process. Determining the point at which ω is maximal over the analyzed portion of the growth curve can be accomplished simply by sorting a column of numbers, as will be familiar to those acquainted with commonly used computer spreadsheet programs, and then identifying the time point or cycle number associated with the maximum angle value in the column. It is unnecessary to calculate derivatives or slopes of curve portions to determine the maximal TArc value.

The TArc values determined in this manner can then be used for quantitative analysis of polynucleotide amounts or concentrations. More particularly, once the TArc values are established for amplification reactions conducted using known amounts of target or calibrator, those data points can be saved, plotted on a graph, or otherwise employed to establish a calibration curve. FIGS. 8-12 represent example calibration curves, because the amplification reactions used for obtaining the results presented therein were conducted using known amounts of the HIV-1 target polynucleotide. Likewise, the TArc value determined for an amplification reaction performed using an unknown starting amount of analyte polynucleotide can be compared with a calibration curve to determine the starting amount of analyte polynucleotide in a sample undergoing testing.

Preferably, a repetitive analysis is carried out over the portion of the curve that includes the upward inflection which indicates the transition from the baseline phase into the growth phase of the curve. In this repetitive analysis, the origin of the first paired set of vectors is located at a first position on the growth curve, and the origin of the second paired set of vectors is located at the next position on the growth curve which corresponds to the next time point. Notably, it is unnecessary to continue the vector analysis over the portion of the curve that includes the convex curvature which characterizes the transition from the growth phase into the plateau phase. Thus, the vector analysis can be limited to the portion of the growth curve that represents a constant percentage of the maximum value achieved on the y-axis for any particular growth curve that would be adequate to exclude that portion of the curve representing a significant transition into the plateau phase. For example, the vector analysis can be restricted to the portion of the growth curve representing no more than 85%, more preferably no more than 75% of the maximum value achieved on the y-axis of the curve. This eliminates the convex curvature leading to the plateau phase as a possible TArc solution. Notably, "convex" curvature refers to a surface that curves outward, and "concave" curvature refers to a surface that curves like the inner surface of a sphere.

Algorithm Employing Directionally Opposed Vectors—OTArc

The vector-based algorithm described above and illustrated below in Example 1 employed paired sets of two vectors that were directionally similar in the x-dimension. More specifically, the directionally similar vectors both extended away from the shared origin in the direction of increasing x-values. This arrangement required the vectors to have different magnitudes in the x-dimension to create the opportunity for an angle therebetween as the two vectors incremented along the growth curve. The algorithm further involved identifying, as a feature of the curve, the point on the x-axis at which the smaller angle between the two vectors became maximal (see FIG. 4). When derived from analysis of reactions conducted using known quantities of an analyte polynucleotide standard, the numerical value of this feature could be plotted against the log of the input target copy number to create a standard curve. Alternatively, if the feature was derived from analysis of a reaction conducted using a test sample, the determined feature could be compared with a standard plot to determine the starting amount or concentration of analyte polynucleotide present in the test sample.

Another vector-based algorithm falling within the scope of the invention similarly involved a reiterative process of establishing paired sets of vectors along a growth curve, but employed directionally opposed vectors instead of directionally similar vectors. Again in contrast with the algorithm employing directionally similar vectors, the algorithm employing directionally opposed vectors did not require both of the vectors in the paired sets to have different magnitudes in the x-dimension, and involved identifying the point along the x-axis at which the angle between two vectors became minimal rather than maximal. In accordance with this latter approach, paired sets of two vectors were established such that they were directionally opposed in the x-dimension relative to the shared origin of the two vectors. In general, one member of a pair of directionally opposed vectors extends from the shared origin in the direction of decreasing x-values, while the other member of the pair extends in the direction of increasing x-values.

Figure 5A:
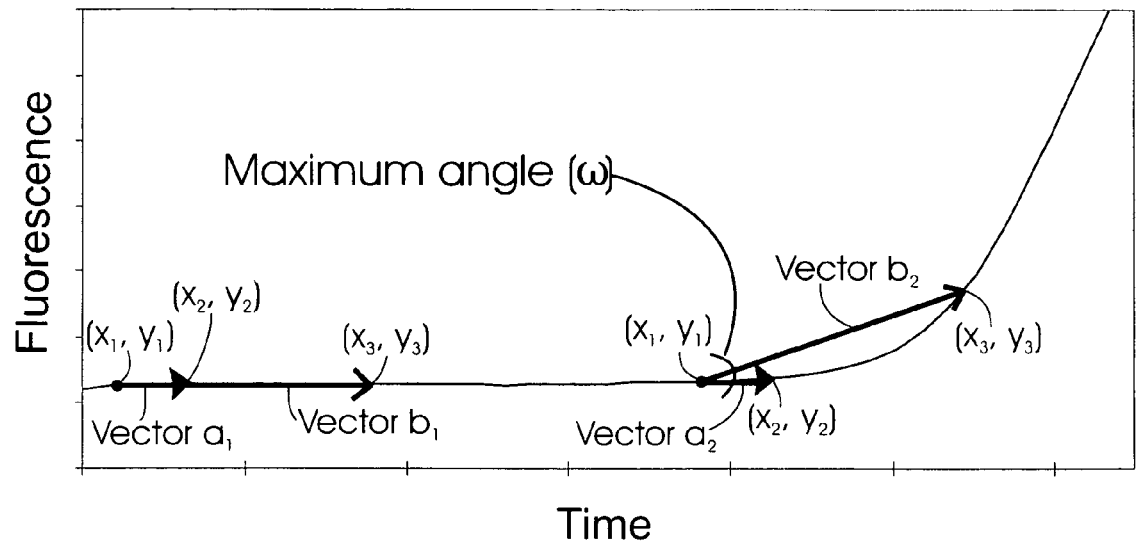
FIGS. 5A-5B schematically illustrate differences between vector-based algorithms employing directionally similar vectors (panel A) and directionally opposed vectors (panel B). In this illustration, "fluorescence" (y-axis) is proportional to the amount of a nucleic acid amplification product present in an in vitro amplification reaction. The time value associated with the point on a growth curve at which the angle between directionally similar vectors becomes a maximum (see panel A) is referred to herein as "TArc." The time value associated with the point on a growth curve at which the angle between directionally opposed vectors becomes a minimum (see panel B) is referred to herein as "OTArc."
Figure 5B:
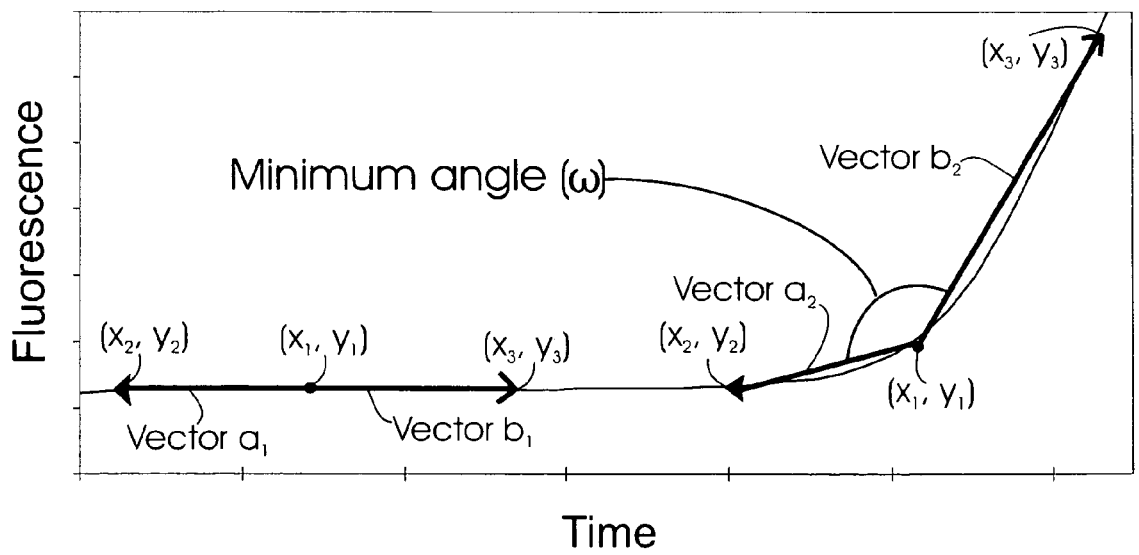

Key aspects of the algorithm which employs directionally opposed vectors, and its relationship to the algorithm which employs directionally similar vectors, can be understood with reference to FIGS. 5A-5B. FIG. 5A schematically illustrates how paired sets of directionally similar vectors can be incremented along the x-dimension of a growth curve, and demonstrates how the angle between the two vectors becomes maximal in the vicinity of the transition between the baseline and growth phases of the growth curve. FIG. 5B schematically illustrates how paired sets of directionally opposed vectors can be incremented along the x-dimension of a growth curve, and demonstrates how the angle between the two vectors becomes minimal in the vicinity of the transition between the baseline and growth phases of the growth curve. Notably, there is no requirement for the vectors to have different magnitudes of their x-components when using the algorithm based on directionally opposed vectors, as illustrated in FIG. 5B. In one preferred embodiment, the magnitudes of the x-components of the two vectors are the same when the analysis is conducted using directionally opposed vectors. In an alternative preferred embodiment, the magnitudes of the x-components of the two vectors are different from each other when the analysis is conducted using directionally opposed vectors.

As shown in FIG. 5B, and in accordance with the algorithm employing directionally opposed vectors, a plurality of paired sets of two vectors are established at different points along the x-dimension of a growth curve. Each of the vectors of a single set of vectors shares the same origin (x1,y1). Also as indicated in the figure, the vectors are established such that their directions are opposed to each other in the x-dimension. When this is the case, the x-coordinate at the head of the first vector (i.e., vector a) has a value less than the value of the x-coordinate at shared origin, and the x-coordinate at the head of the second vector (i.e., vector b) has a value greater than the value of the x-coordinate of the shared origin. Stated differently, when using directionally opposed vectors x2<x1<x3, where x1 is the x-coordinate of the shared origin, where x2 is the x-coordinate at the head of the vector directed toward decreasing x-values, and where x3 is the x-coordinate at the head of the vector directed toward increasing x-values. This arrangement is distinguished from embodiments of the invention which employ directionally similar vectors, wherein x1<x2<x3 (as illustrated in FIG. 2 and FIG. 5A).

Thus, if numerical data representing a growth curve for time-dependent monitoring of amplicon production in a nucleic acid amplification reaction is processed by curve-fitting to result in an optimized equation, that equation can be used to parse the processed growth curve into arbitrary time intervals. For example, these time intervals could be 5 seconds each, 10 seconds each, or other desired time or cycle number interval. Continuing with this example, the magnitudes of the x-components of the directionally opposed vectors could be arbitrarily set to 50 seconds. In such a case, the origin of a first paired set of vectors could be established at x1=50 seconds, the head of the first vector would then be positioned at x2=0 seconds, and the head of the directionally opposed second vector would be positioned at x3=100 seconds. As described above, a second paired set of vectors would increment along the x-dimension of the growth curve such that the origin of the second paired set of vectors was established at x1=55 seconds, and the process repeated as desired. Table 2 illustrates how the x-components of paired sets of directionally opposed vectors would increment in the reiterative process of establishing paired sets of vectors, with "x1" being the value of the x-coordinate of the shared origin, "x2" being the value of the x-coordinate at the head of the first vector, and "x3" being the value of the x-coordinate at the head of the second vector.

TABLE 2

Incrementing the X-Component of Directionally Opposed Vector Sets

| Increment No. | X1 (sec) | X2 (sec) | X3 (sec) |
|---|---|---|---|
| 1 | 50 | 0 | 100 |
| 2 | 55 | 5 | 105 |
| 3 | 60 | 10 | 110 |
| 4 | 65 | 15 | 115 |
| 5 | 70 | 20 | 120 |
| N | n | n − 50 | n + 50 |

The values of the y-coordinates of the vectors preferably are determined either directly from experimental data, or more preferably calculated using a moving average smoothing function, or a curve-fitting operation. When curve-fitting is used, values of the y-coordinates of the vectors preferably are calculated by solving optimized equations using techniques described herein, or other techniques that will be familiar to those having an ordinary level of skill in the art. With the x- and y-coordinates of the different paired sets of vectors established, the angles between the vectors can be calculated using standard mathematical approaches, such as the above-described equation (1), and the calculated angles associated with different time points along the x-dimension of the growth curve. In accordance with the algorithm employing directionally opposed vectors, determining the time component associated with the origin of the vector pair having the minimum angle will identify the feature of the curve (i.e., the OTArc) to be plotted against the input log target copy number to create a standard curve, or to be compared with a standard curve to identify the amount or concentration of polynucleotide analyte in a test sample.

Notably, the two approaches schematized in the different panels of FIG. 5 identify different features of the same curve. More specifically, the analysis employing directionally similar vectors identifies a point on the curve which precedes, at least slightly, the maximum concave curvature in the transition separating the baseline and growth phases. In contrast, analyses based on the use of directionally opposed vectors identify a feature of the curve which occurs slightly later in the x-dimension, and which is associated more closely with the maximum concave inflection within the transition between the baseline and growth phases. FIG. 6 illustrates this by showing a raw data growth curve (i.e., not processed by any smoothing algorithm) for a nucleic acid amplification reaction, and indicates the identified points on the curve for TArc, OTArc, the maximum of the second derivative, and the maximum of the first derivative. Of course, the TArc and OTArc values represent the time values on the x-axis associated with the points indicated on the growth curve.

Smoothing Growth Curve Data Prior to Vector Analysis

To ensure robustness of the disclosed vector analysis algorithms, methods were sought to improve the quality of growth curve data used in the analyses. More particularly, methods of smoothing the growth curves using either moving averages or curve-fitting techniques were used for this purpose.

Smoothing by Moving Averages

Moving averages were used to minimize the impact of statistical fluctuations or "noise" in the growth curve data applied equally throughout the curve. The moving averages smoothing function takes the average of a set of values around a particular value in a list. In one embodiment, a moving average of five sequential data points representing fluorescence measurements was used. This procedure adjusted the fluorescence measurements which subsequently were used as a new data set for the growth curve. Table 3 illustrates calculation of the moving average for a set of seven data points.

TABLE 3

Illustrative Calculation of a Moving Average

| Time Point | Signal Value | Moving Average |
|---|---|---|
| 1 | A1 | |
| 2 | A2 | |
| 3 | A3 | (A1 + A2 + A3 + A4 + A5)/5 |
| 4 | A4 | (A2 + A3 + A4 + A5 + A6)/5 |
| 5 | A5 | (A3 + A4 + A5 + A6 + A7)/5 |
| 6 | A6 | |
| 7 | A7 | |

The vector analysis described herein was used to analyze time-dependent fluorescence data that had been obtained in real-time nucleic acid amplification reactions, and that had been smoothed by the moving average technique. Notably, the moving average technique did not yield an equation that defined the growth curve.

Smoothing by Curve-Fitting

Another method of smoothing growth curve data used in the vector analysis involved deriving an equation that defined a growth curve using a procedure referred to as "curve-fitting." In this approach, one of several candidate equations served as a basic mathematical model for the growth curve. Each of the different equations included variables that characterized different growth curve parameters. After estimating the values of these variables, using no more than routine modeling procedures familiar to those having an ordinary level of skill in the art, a reiterative process of modifying the estimated values to obtain an equation defining the curve was executed using commercially available curve-fitting software. All of the curve-fitting described herein particularly employed the SOLVER program available as an EXCEL add-in tool for finding an optimal value for a formula, and equation solving from Microsoft Corporation, (Redmond, Wash.). However, other commercially available curve-fitting programs also can be used for establishing a best-fit curve successfully. The curve-fitting procedures used herein yielded equations that defined a subject growth curve, or a portion thereof.

The equations deduced by curve-fitting were used to parse the growth curves into time intervals, to determine the magnitude of amplicon signals as a function of the parsed time intervals, and to draw paired sets of vectors and determine TArc or OTArc values in accordance with the above-described vector analysis methods. Curve-fitting of data that relates the amount of analyte amplicon synthesized as a function of time, or cycle number, can be carried out using different mathematical models. Notably, because this procedure yields an equation defining the growth curve, it is possible to perform vector analysis using arbitrarily parsed time intervals. Thus, even if fluorescent readings in a real-time amplification procedure were only collected at 30 second intervals, the equation derived from the curve-fitting procedure allows for parsing into arbitrary intervals, such as 5 second intervals.

Curve-Fitting: Model A

One embodiment of the curve-fitting procedure began with a polynomial equation such as that described by Weusten et al., in *Nucleic Acids Res. Vol.* 30, No. 6e26, pp. 1-7 (2002), or a modification thereof. The first model used to demonstrate how curve-fitting could be used in connection with the invention involved a four-point curve-fit, and was defined by equation (3).

$$R(t) = Y_0 + a1 a2 [e^{a2(t-a3)}/(1+e^{a2(t-a3)})] \ln(1+e^{a2(t-a3)}) \quad (3)$$

In equation (3), R(t) represents the polynucleotide level (i.e., the amount or concentration) at a particular time point; $Y_0$ represents the background signal (i.e., the baseline fluorescent signal prior to a growth phase); a1 and a2 are parameters describing growth; and a3 defines the location of the curvature marking the transition into the growth phase of the curve. Notably, a1a2 is the slope of the log-linear portion of the curve, and so is associated with the rate of amplicon formation. A reiterative process of adjusting the values of the different variables was carried out using the SOLVER program, making the following initial estimates for each of the variables: $Y_0$ was estimated to be 0.1 RFU (Relative Fluorescence Units); a1 was estimated to be 0.05, and a2 was estimated to be 1. These estimates were held fixed for all calculations. The value of the a3 variable was estimated to be 3 minutes less than the time needed to achieve 25% of the maximum fluorescence signal measured during the course of any particular amplification reaction. The initial estimate for the $Y_0$ variable was based on a global minimum function applied to all curves, with the lowest value being defined as zero on the y-axis. The initial estimate approximated the baseline fluorescence signal, accounting for baseline stabilization and an observed level of fluctuation commonly referred to as "noise." The initial estimate for a3 was based on the routine observation that 25% of the maximum fluorescence signal measured during the course of any particular amplification reaction ensured that the signal was in a portion of the curve above the background fluorescence signal, and that subtracting 3 minutes from this time value ensured a position nearer to the beginning of the growth phase of the curve. Initial static estimates for the a1 and a2 variables were based on the finding that SOLVER software was able to optimize final values for a1 and a2 when initial estimates for $Y_0$ and a3 closely approximated the optimized values for $Y_0$ and a3. Simply stated, when the initial estimates for $Y_0$ and a3 closely approximated the final values for $Y_0$ and a3, the SOLVER software was able to optimize, through a reiterative process, values for a1 and a2 even when initial estimates for a1 and a2 were less than ideal.

Since the determination of TArc and OTArc values required analysis of the transition from the baseline phase into the growth phase of the subject curve, it was unnecessary to perform curve-fitting on the portion of a curve represented by, and following the convex transition from the growth phase into the plateau phase. Thus, the procedure was simplified by performing curve-fitting on only 75% of the growth curve data. More specifically, only the data representing 0-75% of the maximum amplitude of the measured fluorescent signal measured in the real-time amplification procedure was used for curve-fitting. Analysis of the upper portion of the curve was not required for calculating either TArc or OTArc values. As indicated above, reiterative computing techniques were used to establish values for each of the four variables such that an equation substantially conforming to the growth curve represented by the experimental data resulted.

Curve-Fitting: Model B

To prove that success of the vector-based analytical method did not depend on the use of any particular mathematical model to carry out the curve-fitting procedure, another mathematical model also was employed. In this second instance, the commercially available TABLECURVE software package (SYSTAT Software Inc.; Richmond, Calif.) was used to identify and select an equation that described exemplary real-time nucleic acid amplification curves. The resulting equation, used for mathematical modeling (referred to herein as "Model B"), was given by:

$$R(t)=a+b(1-\exp(-(t-d*\ln(1-2^{-(-1/e)})-c)/d))^{-e} \quad (4)$$

In equation (4), R(t) represents the polynucleotide level (i.e., the amount or concentration) at a particular time point. The five parameters in equation (4) were: "a", "b", "c", "d", and "e". The variable "t" represented time. Similar to the approach described above, Model B was optimized for each data set using the SOLVER program available as an EXCEL add-in tool from Microsoft Corporation (Redmond, Wash.). Initial estimates were used, but were not optimized to the extent described under the discussion of Model A.

In accordance with Model B, the data from real-time amplification reactions representing 85% of the maximum fluorescence signal measured during the course of the reaction was used in the analysis. This simplification was possible because it was unnecessary to use portions of the growth curves representing the convex transition into the plateau phase to identify either TArc or OTArc values.

Curve-Fitting: Model C

To demonstrate even further that success of the vector-based analytical method did not depend on the use of any particular mathematical model to carry out the curve-fitting procedure, yet another mathematical model also was employed. As described above, the TABLECURVE software package was again used to identify and select an equation that described exemplary real-time nucleic acid amplification curves. The resulting equation, used for mathematical modeling (referred to herein as "Model C"), was given by:

$$R(t)=a+b/(1+\exp(-(t-d*\ln(2^{(1/e)}-1)-c)/d))^{-e} \quad (5)$$

In equation (5), R(t) represents the polynucleotide level (i.e., the amount or concentration) at a particular time point. The five parameters in equation (5) were: "a", "b", "c", "d", and "e". The variable "t" represented time. Similar to the approach described above, Model C was optimized for each data set using the SOLVER program available as an EXCEL add-in tool from Microsoft Corporation (Redmond, Wash.). Initial estimates were used, but were not optimized to the extent described under the discussion of Model A.

In accordance with Model C, the data from real-time amplification reactions representing 80% of the maximum fluorescence signal measured during the course of the reaction was used in the analysis. Again, this simplification was possible because it was unnecessary to use portions of the growth curves representing the convex transition into the plateau phase to identify either TArc or OTArc values.

Optional Subtraction of a Global Minimum

Those having an ordinary level of skill in the art will appreciate that virtually all nucleic acid detection systems are associated with some level of detectable background signal in the absence of any nucleic acid amplification. This background may, for example, result from natural fluorescence characteristics of the vessel containing the reaction mixture being analyzed for appearance of amplicons. When background fluorescence in a procedure is significant, a global minimum subtraction step preferably is carried out by finding a global minimum, and then subtracting this value from all data points representing the signal for amplicon detection. When this is done, the resulting signals for amplicon amount present at the different time points can be compared with each other directly. Thus, global minimum subtraction facilitates universal and static $Y_0$ predictions or estimates. It is to be understood that a global minimum is the lowest measured value among a collection of measurements.

The advantages of performing the global minimum subtraction are particularly noteworthy in the context of multiplex amplification and detection reactions that employ different fluorescent dyes. Typically, different fluorescent dyes are characterized by different levels of background fluorescence.

Apparatus for Implementing the Vector-Based Algorithm

The vector-based algorithms disclosed herein are conveniently implemented using a computer or similar processing device ("computer" hereafter). In different preferred embodiments, software or machine-executable instructions for performing an algorithm can be loaded or otherwise held in a memory component of a freestanding computer, or in a memory component of a computer linked to a device used for monitoring, preferably as a function of time, the amount of a product undergoing analysis. In a highly preferred embodiment, software for executing the vector-based algorithm is held in a memory component of a computer that is linked to, or that is an integral part of a device capable of monitoring the amount of an amplicon present in a reaction mixture as a function of time.

Indeed, either or both of a controller system for controlling a real-time amplification device and/or the detection system of the real-time amplification device can be coupled to an appropriately programmed computer which functions to instruct the operation of these instruments in accordance with preprogrammed or user input instructions. The computer preferably also can receive data and information from these instruments, and interpret, manipulate and report this information to the user.

In general, the computer typically includes appropriate software for receiving user instructions, either in the form of user input into a set of parameter fields, or in the form of preprogrammed instructions (e.g., preprogrammed for a variety of different specific operations). The software then converts these instructions to appropriate language for instructing the operation of the real-time amplification controller to carry out the desired operation. The computer also is capable of receiving data from the one or more sensors/detectors included within the system, and interprets the data in accordance with the programming. The system preferably includes software that correlates a feature of a growth curve representing the quantity of amplified copies of the nucleic acid of interest as a function of time, as detected by the detector, to the number of copies of the nucleic acid of interest present in a test sample.

When the computer used for executing the vector-based algorithm is an integral component of an apparatus for performing and analyzing real-time nucleic acid amplification reactions, the apparatus preferably comprises a temperature-controlled incubator, a detection device for collecting signals, an analyzing device (e.g., a computer or processor) for analyzing signals and an output device for displaying data obtained or generated by the analyzing device. The analyzing device may be connected to the temperature-controlled incubator through an input device known in the art, and/or connected to an output device known in the art for data display. In one embodiment, the temperature-controlled incubator is capable of temperature cycling.

Generally speaking, the various components of an apparatus for performing the real-time nucleic acid amplification useful in connection with the vector-based algorithm will be conventional components that will be familiar to those having an ordinary level of skill in the art. The temperature-controlled incubator used to perform and analyze real-time nucleic acid amplification may be of a conventional design which can hold a plurality of reaction tubes, or up to 96 reaction samples in a temperature-controlled block in standard amplification reaction tubes or in wells of a multiwell plate. In one aspect, the detection system is suitable for detecting optical signals from one or more fluorescent labels. The output of the detection system (e.g., signals corresponding to those generated during the amplification reaction) can be fed to the computer for data storage and manipulation. In one embodiment, the system detects multiple different types of optical signals, such as multiple different types of fluorescent labels and has the capabilities of a microplate fluorescence reader. The detection system is preferably a multiplexed fluorimeter containing an excitation light source, which may be a visible light laser or an ultraviolet lamp or a halogen lamp or a light-emitting diode (LED), a multiplexer device for distributing the excitation light to the individual reaction tubes and for receiving fluorescent light from the reaction tubes, a filtering means for separating the fluorescence light from the excitation light by their wavelengths, and a detection means for measuring the fluorescence light intensity. Preferably, the detection system of the temperature-controlled incubator provides a broad detection range that allows flexibility of fluorophore choice, high sensitivity and excellent signal-to-noise ratio. Optical signals received by the detection system are generally converted into signals which can be operated on by the processor to provide data which can be viewed by a user on a display of a user device in communication with the processor. The user device may comprise a user interface or may be a conventional commercially available computer system with a keyboard and video monitor. Examples of data which can be displayed by the user device include amplification plots, scatter plots, sample value screens for all the tubes or reaction vessels in the assembly and for all labels used, an optical signal intensity screen (e.g., fluorescent signal intensity screen), final call results, text reports, and the like.

Application of the Vector-Based Algorithm to Quantitation of Polynucleotides

In accordance with one embodiment, a method for quantifying an analyte is described, wherein the analyte is a polynucleotide. The method comprises the steps of contacting the analyte with an amplifying agent (and all compounds needed to amplify at least a part of the analyte) and amplifying at least a part of the analyte to result in the formation of analyte amplicons. Typically, only a limited region of the analyte is amplified. More specifically, the sequence of the analyte polynucleotide flanked by two amplification oligonucleotides is amplified in the reaction. The amount of amplification product is then determined as a function of reaction time, and a vector analysis of the time-dependent amplicon formation performed to determine a feature which indicates a transition from a baseline phase to a growth phase of a growth curve describing the reaction. Although the quantitative relationship between the amount of amplification product and the reaction time is conveniently visualized in the form of a growth curve on a two-dimensional graph, the vector analysis typically is carried out by a computer or data processor using only numerical data. In one preferred embodiment the amplification product is detected by means of fluorescence and the amplification product is formed in a TMA, NASBA, PCR, or SDA reaction. In the context of this invention, determining the amount of amplification product as a function of time does not mean that the absolute amount of amplification product needs to be measured. Instead, it is sufficient to determine relative signals, since relative determination allows for performance of the vector analysis to determine the feature of the growth curve, which according to the invention may then be used to determine the absolute amount or concentration of the initial analyte polynucleotide present in the amplification reaction.

To illustrate more particularly how the disclosed vector-based algorithm can be applied to the quantitation of nucleic acids using real-time amplification methods, a single set of data was selected for assessment using either: (1) vector-based analysis of raw data, (2) vector-based analysis of data smoothed by calculation of moving averages, or (3) vector-based analysis of data having been produced by curve-fitting of the experimental data using mathematical modeling.

Example 1 describes how the vector-based algorithm employing directionally similar vectors was used to analyze results from real-time nucleic acid amplification reactions.

Example 1

Application of the Vector-Based Analytical Method Using Directionally Similar Vectors A series of TMA reactions were performed using from $5 \times 10^1$ to $5 \times 10^5$ copies of an HIV-1 subtype B analyte RNA, and a molecular torch specific for the amplicon. Fluorescence signals indicating amplicon synthesis were monitored as a function of time, and the results plotted on the graph shown in FIG. 7. In this procedure, fluorescence readings indicative of the amount of amplicon present in the amplification reaction mixture were taken every 19.4 seconds, approximately. The result set represented in the figure was processed using the disclosed algorithm employing directionally similar vectors under different conditions of data smoothing.

The vector-based algorithm employed in these analyses involved establishing paired sets of vectors, with each vector of a set sharing a common origin along the data points represented on a growth curve. The vectors within a set had different x-component magnitudes, so that the vectors had different directions in the vicinity of the transition between the baseline and growth phases of the growth curves. To simplify the analysis, only the data points preceding the transition into the plateau phase of the growth curves (i.e., representing about 75% of the maximum fluorescent reading) were used in the calculations. Angles between the different vector sets were calculated, and the time associated with the vector set giving rise to the greatest angle identified as the TArc. This is illustrated in FIG. 5A. The TArc values were then plotted against the log of the input copy number, and the parameters of a best fit line or curve determined. When an internal calibrator was used, the relationship between target and internal calibrator was plotted against the log of the input target copy number, and the parameters of the best fit line or curve determined.

Applications of this analytical method to the experimental data, whether unprocessed or processed to achieve smoothing, are described below. In all instances, amplification reactions were performed in replicates of six, and the results from these replicates used for statistical analysis. In no case did a trial conducted in the absence of added analyte polynucleotide produce a result that exceeded a minimum range criterion necessary to be considered indicative of the presence of the analyte. Thus, there were no false positives observed in the procedure.

Raw Experimental Data

Figure 7:
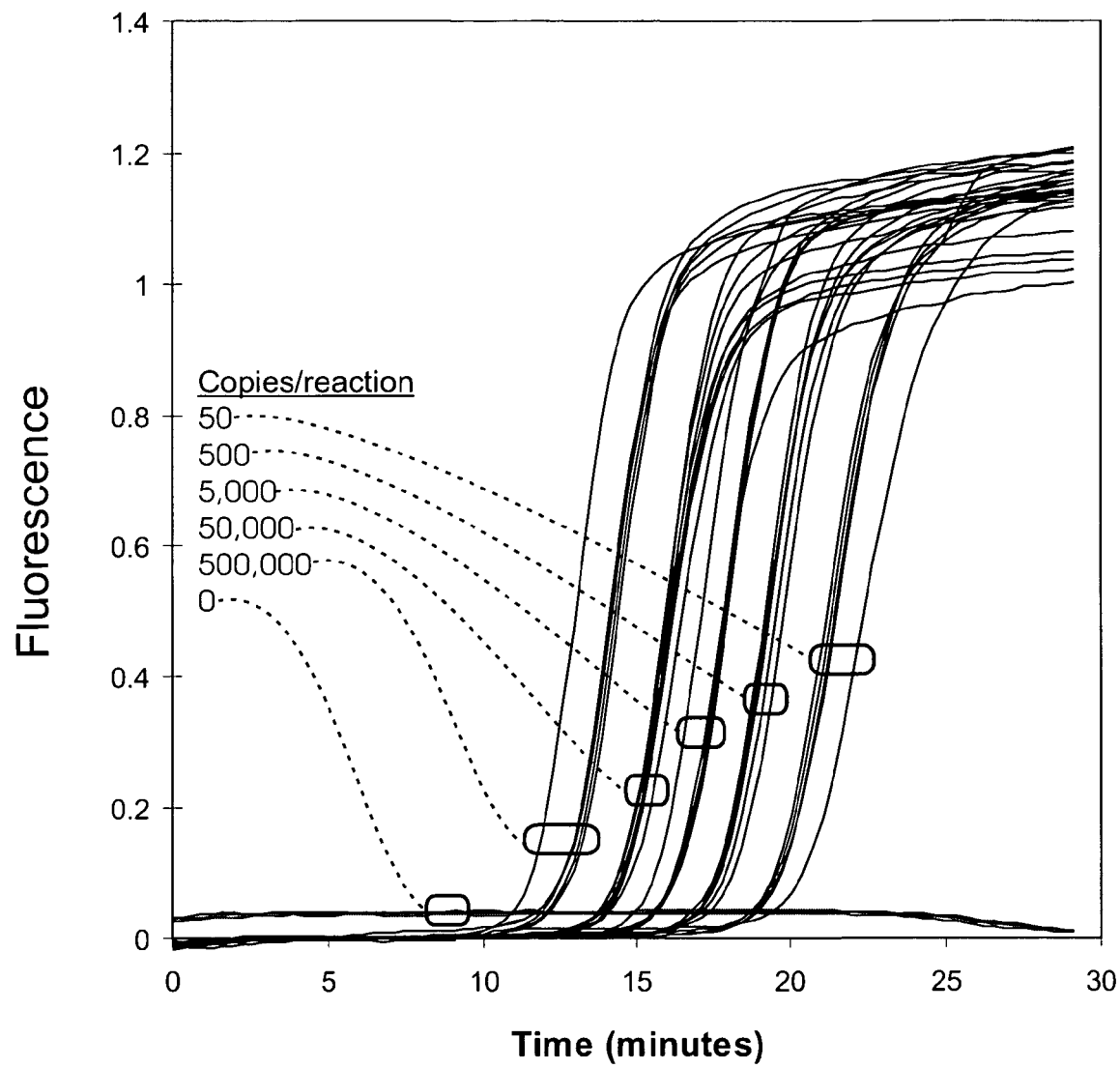
FIG. 7 shows a series of growth curves representing the amount of nucleic acid amplification product (measured by fluorescence signal) as a function of time for nucleic acid amplification reactions conducted using varying amounts of input HIV-1 analyte polynucleotide (indicated by "copies/reaction").

The vector-based algorithm was applied directly to the analysis of the raw data used to produce the results shown in FIG. 7. TArc values were determined for each of the curves generated at each level of analyte polynucleotide tested, and those results plotted on the graph shown in FIG. 8. A summary of the results plotted in the figure appear in Table 4.

TABLE 4

Summary of the Analysis Performed Using the Vector-Based Algorithm on Raw Experimental Data

| Input Target Amt. (copy no.) | Avg. TArc | Std. Dev. TArc | Avg. Log Copy No. | Std. Dev. Log Copy No. |
|---|---|---|---|---|
| 0 | NA | NA | NA | NA |
| $5 \times 10^1$ | 19.5 | 1.07 | 1.67 | 0.61 |
| $5 \times 10^2$ | 17.5 | 0.82 | 2.63 | 0.13 |
| $5 \times 10^3$ | 15.5 | 0.79 | 3.93 | 0.45 |
| $5 \times 10^4$ | 14.4 | 0.17 | 4.54 | 0.10 |
| $5 \times 10^5$ | 12.4 | 0.53 | 5.72 | 0.30 |

NA: Not applicable

Figure 8:
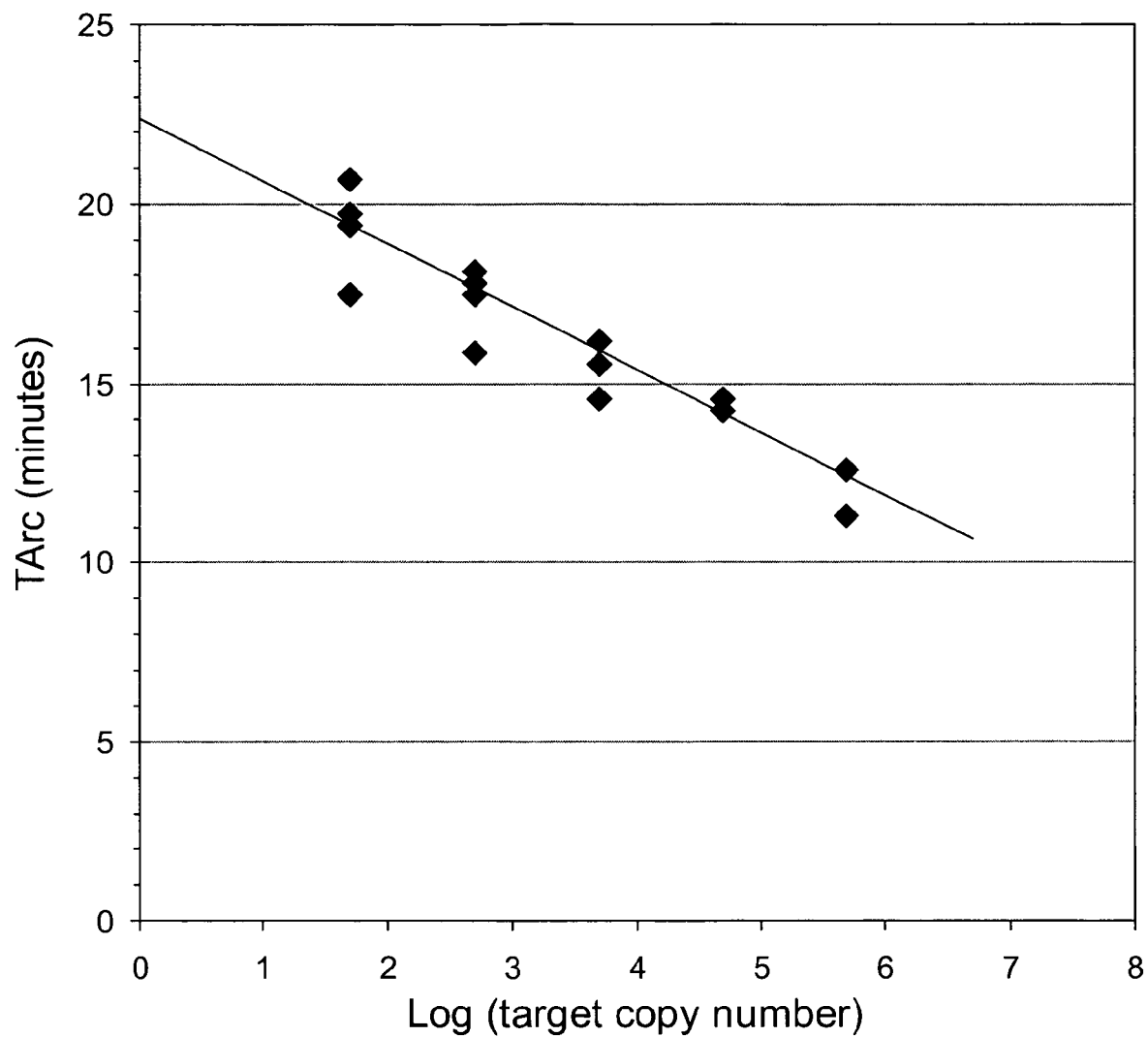
FIG. 8 is a graph showing results from a vector-based analysis of the raw experimental data appearing in FIG. 7 (no smoothing function). The graph relates the amount of an HIV-1 analyte polynucleotide standard that was input into a real-time nucleic acid amplification reaction (x-axis) and the calculated TArc time (y-axis). Data points (filled diamonds) represent calculated TArc values for individual growth curves.

As indicated by the results presented in Table 4 and in FIG. 8, there was a strong relationship between the determined TArc values and the log of the input template copy number. Scatter among the data points plotted in FIG. 8 resulted from variation among the data plotted in the curves of FIG. 7. Clearly, the disclosed algorithm could be used to process raw experimental data that had not been smoothed by calculation of moving averages or by curve-fitting, to yield a relationship between the amount of template input into an amplification reaction and the determined TArc value. Parameters of the line determined using the TArc values appear in Table 9.

Smoothing by Moving Averages

The vector-based algorithm was applied to the analysis of data that had first been smoothed by calculation of a moving average over five adjacent data points. TArc values were determined for each of replicate curves generated at each level of analyte polynucleotide tested, and those results plotted on the graph shown in FIG. 9. A summary of the results plotted in the figure appear in Table 5.

TABLE 5

Summary of the Analysis Performed Using the Vector-Based Algorithm on Experimental Data Smoothed by 5-Point Moving Average

| Input Target Amt. (copy no.) | Avg. TArc | Std. Dev. TArc | Avg. Log Copy No. | Std. Dev. Log Copy No. |
|---|---|---|---|---|
| 0 | NA | NA | NA | NA |
| $5 \times 10^1$ | 19.4 | 1.00 | 1.58 | 0.19 |
| $5 \times 10^2$ | 17.4 | 0.80 | 2.71 | 0.15 |
| $5 \times 10^3$ | 15.5 | 0.88 | 3.95 | 0.48 |
| $5 \times 10^4$ | 14.3 | 0.17 | 4.57 | 0.09 |
| $5 \times 10^5$ | 12.3 | 0.52 | 5.67 | 0.28 |

NA: Not applicable

Figure 9:
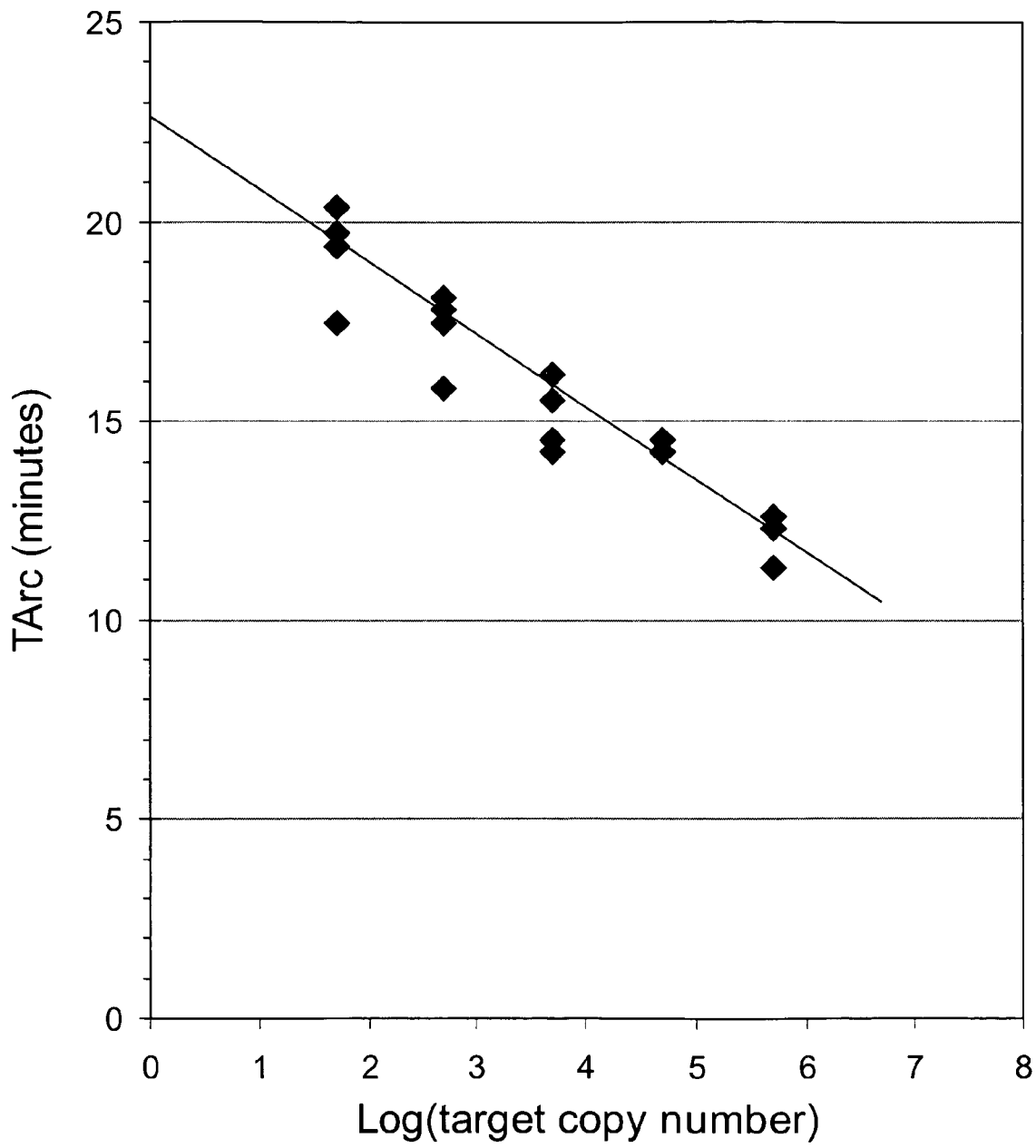
FIG. 9 is a graph showing results from a vector-based analysis of experimental data appearing in FIG. 7 after processing using a moving average smoothing function. The graph relates the amount of an HIV-1 analyte polynucleotide standard that was input into a real-time nucleic acid amplification reaction (x-axis) and the calculated TArc time (y-axis). Data points (filled diamonds) represent calculated TArc values for individual growth curves.

As indicated by the results presented in Table 5 and in FIG. 9, there was a strong relationship between the determined TArc values and the log of the input template copy number. Again, scatter among the data points plotted in the figure resulted from variation among the data plotted in the curves of FIG. 7. Clearly, the disclosed algorithm could be used to process raw experimental data that had been smoothed by calculation of moving averages to yield a relationship between the amount of template input into an amplification reaction and the determined TArc value. Parameters of the line determined using the TArc values appear in Table 9.

Smoothing by Curve-Fitting (Model A)

The vector-based algorithm was applied to the analysis of data that had been used to establish an equation by curve-fitting. In a first example of this technique, a four-point curve-fit was carried out for each data set using equation (3), described above. Initial estimates for the different variables are given above in connection with the discussion of this mathematical model. A reiterative process of adjusting the values of the different variables was carried out to determine an equation for each curve, also as described above. Thereafter, the growth curve represented by the equation was parsed into 5 second time units, and the vector analysis conducted using these time points as the origins for a series of vectors, in accordance with the disclosed algorithm. TArc values were determined for each of the replicate curves generated at each level of analyte polynucleotide tested, and those results plotted on the graph shown in FIG. 10. A summary of the results plotted in the figure appear in Table 6.

TABLE 6

Summary of the Analysis Performed Using the Vector-Based Algorithm on Experimental Data Smoothed by Curve-Fitting Model A

| Input Target Amt. (copy no.) | Avg. TArc | Std. Dev. TArc | Avg. Log Copy No. | Std. Dev. Log Copy No. |
|---|---|---|---|---|
| 0 | NA | NA | NA | NA |
| $5 \times 10^1$ | 19.0 | 0.90 | 1.64 | 0.54 |
| $5 \times 10^2$ | 17.2 | 0.76 | 2.72 | 0.46 |
| $5 \times 10^3$ | 15.3 | 0.89 | 3.85 | 0.53 |
| $5 \times 10^4$ | 14.1 | 0.13 | 4.57 | 0.08 |
| $5 \times 10^5$ | 12.2 | 0.46 | 5.72 | 0.28 |

NA: Not applicable

Figure 10:
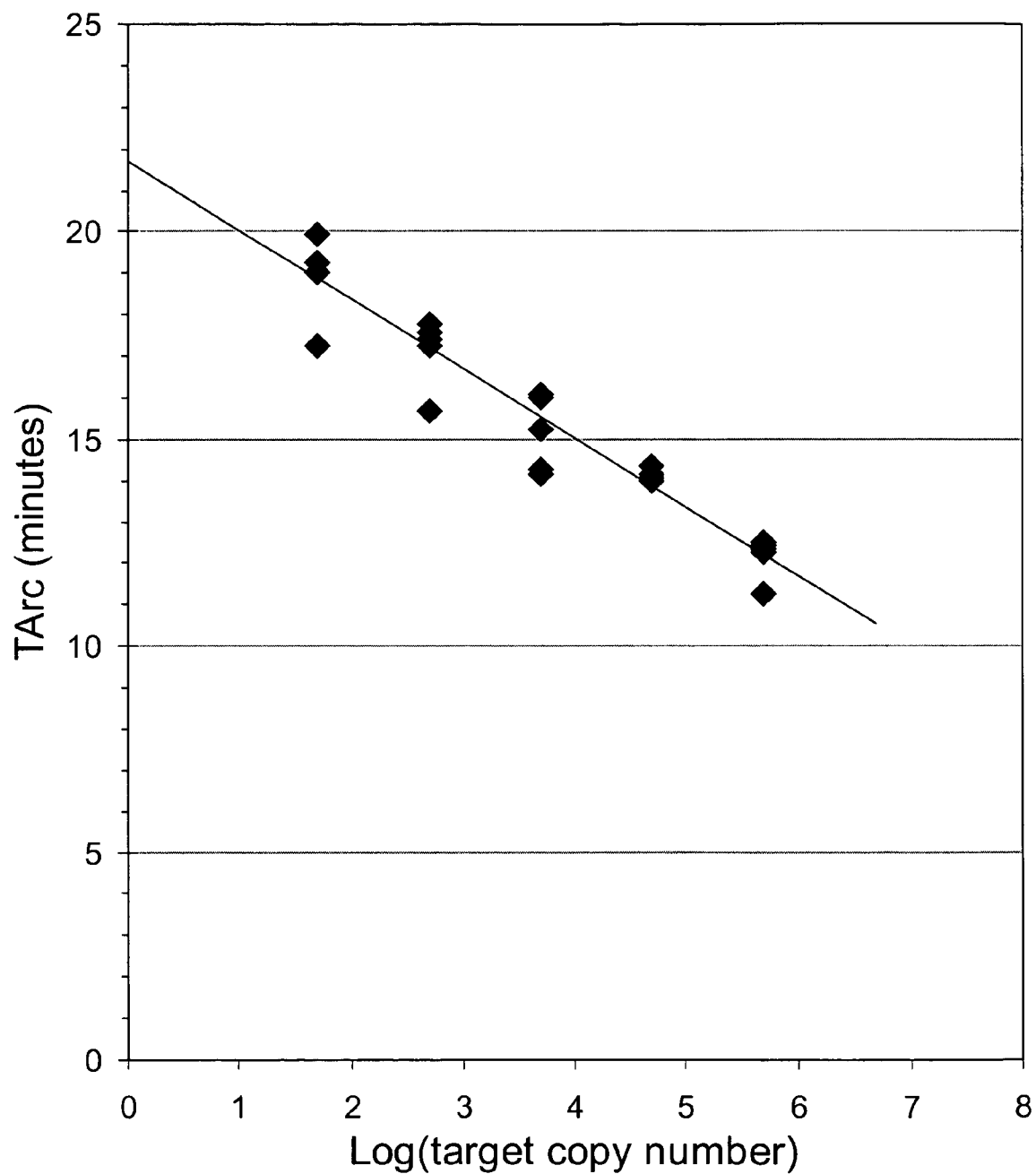
FIG. 10 is a graph showing results from a vector-based analysis of experimental data appearing in FIG. 7 after processing using a curve-fitting smoothing function (equation 3, below). The graph relates the amount of an HIV-1 analyte polynucleotide standard that was input into a real-time nucleic acid amplification reaction (x-axis) and the calculated TArc time (y-axis). Data points (filled diamonds) represent calculated TArc values for individual growth curves.

As indicated by the results presented in Table 6 and in FIG. 10, there was a strong relationship between the determined TArc values and the log of the input template copy number. Scatter among the data points plotted in FIG. 10 resulted from variation among the data plotted in the curves of FIG. 7. Clearly, the disclosed algorithm could be used to process experimental data that had been smoothed by a first curve-fitting approach to yield a relationship between the amount of template input into an amplification reaction and the determined TArc value. Parameters of the line determined using the TArc values appear in Table 9.

Smoothing by Curve-Fitting (Model B)

The vector-based algorithm was next applied to the analysis of data that had been used to establish an equation by an alternative curve-fitting operation. In this second example of the technique, a five-point curve-fit was carried out for each data set using equation (4), described above. As indicated above in connection with the discussion of this mathematical model, initial estimates for the different variables were used, and a reiterative process of adjusting the values of the different variables was carried out to determine an equation for each curve. Thereafter, the growth curve represented by the equation was parsed into 5 second time units, and the vector analysis conducted using these time points as the origins for a series of vectors, in accordance with the disclosed algorithm. TArc values were determined for each of the replicate curves generated at each level of analyte polynucleotide tested, and those results plotted on the graph shown in FIG. 11. A summary of the results plotted in the figure appear in Table 7.

TABLE 7

Summary of the Analysis Performed Using the Vector-Based Algorithm on Experimental Data Smoothed by Curve-Fitting Model B

| Input Target Amt. (copy no.) | Avg. TArc | Std. Dev. TArc | Avg. Log Copy No. | Std. Dev. Log Copy No. |
|---|---|---|---|---|
| 0 | NA | NA | NA | NA |
| $5 \times 10^1$ | 18.9 | 0.92 | 1.67 | 0.55 |
| $5 \times 10^2$ | 17.2 | 0.80 | 2.70 | 0.48 |
| $5 \times 10^3$ | 15.3 | 0.92 | 3.86 | 0.55 |
| $5 \times 10^4$ | 14.2 | 0.18 | 4.51 | 0.11 |
| $5 \times 10^5$ | 12.1 | 0.53 | 5.76 | 0.32 |

NA: Not applicable

Figure 11:
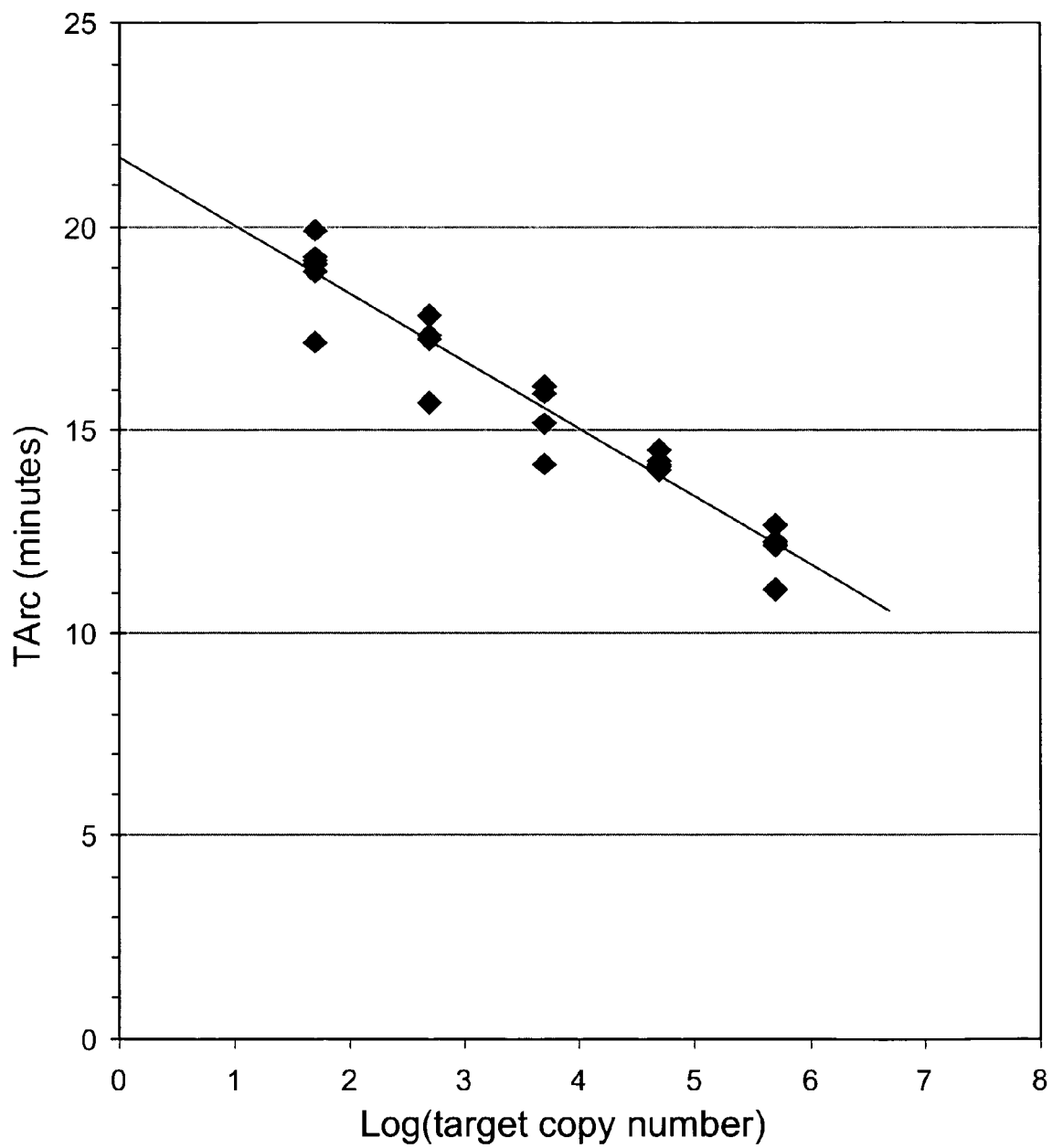
FIG. 11 is a graph showing results from a vector-based analysis of experimental data appearing in FIG. 7 after processing using a curve-fitting smoothing function (equation 4, below). The graph relates the amount of an HIV-1 analyte polynucleotide standard that was input into a real-time nucleic acid amplification reaction (x-axis) and the calculated TArc time (y-axis). Data points (filled diamonds) represent calculated TArc values for individual growth curves.

As indicated by the results presented in Table 7 and in FIG. 11, there was a strong relationship between the determined TArc values and the log of the input template copy number. Scatter among the data points plotted in FIG. 11 resulted from variation among the data plotted in the curves of FIG. 7. Clearly, the disclosed algorithm could be used to process experimental data that had been smoothed by a first curve-fitting approach to yield a relationship between the amount of template input into an amplification reaction and the determined TArc value. Parameters of the line determined using the TArc values appear in Table 9.

Smoothing by Curve-Fitting (Model C)

The vector-based algorithm was next applied to the analysis of data that had been used to establish an equation by yet another curve-fitting operation. In this third example of the technique, a five-point curve-fit was carried out for each data set using equation (5), described above. As indicated above in connection with the discussion of this mathematical model, initial estimates for the different variables were used, and a reiterative process of adjusting the values of the different variables was carried out to determine an equation for each curve. Thereafter, the growth curve represented by the equation was parsed into 5 second time units, and the vector analysis conducted using these time points as the origins for a series of vectors, in accordance with the disclosed algorithm. TArc values were determined for each of the replicate curves generated at each level of analyte polynucleotide tested, and those results plotted on the graph shown in FIG. 12. A summary of the results plotted in the figure appear in Table 8.

TABLE 8

Summary of the Analysis Performed Using the Vector-Based Algorithm on Experimental Data Smoothed by Curve-Fitting Model C

| Input Target Amt. (copy no.) | Avg. TArc | Std. Dev. TArc | Avg. Log Copy No. | Std. Dev. Log Copy No. |
|---|---|---|---|---|
| 0 | NA | NA | NA | NA |
| $5 \times 10^1$ | 19.0 | 0.91 | 1.64 | 0.54 |
| $5 \times 10^2$ | 17.1 | 0.74 | 2.74 | 0.44 |
| $5 \times 10^3$ | 15.3 | 0.89 | 3.84 | 0.53 |
| $5 \times 10^4$ | 14.1 | 0.16 | 4.53 | 0.09 |
| $5 \times 10^5$ | 12.1 | 0.51 | 5.74 | 0.30 |

NA: Not applicable

Figure 12:
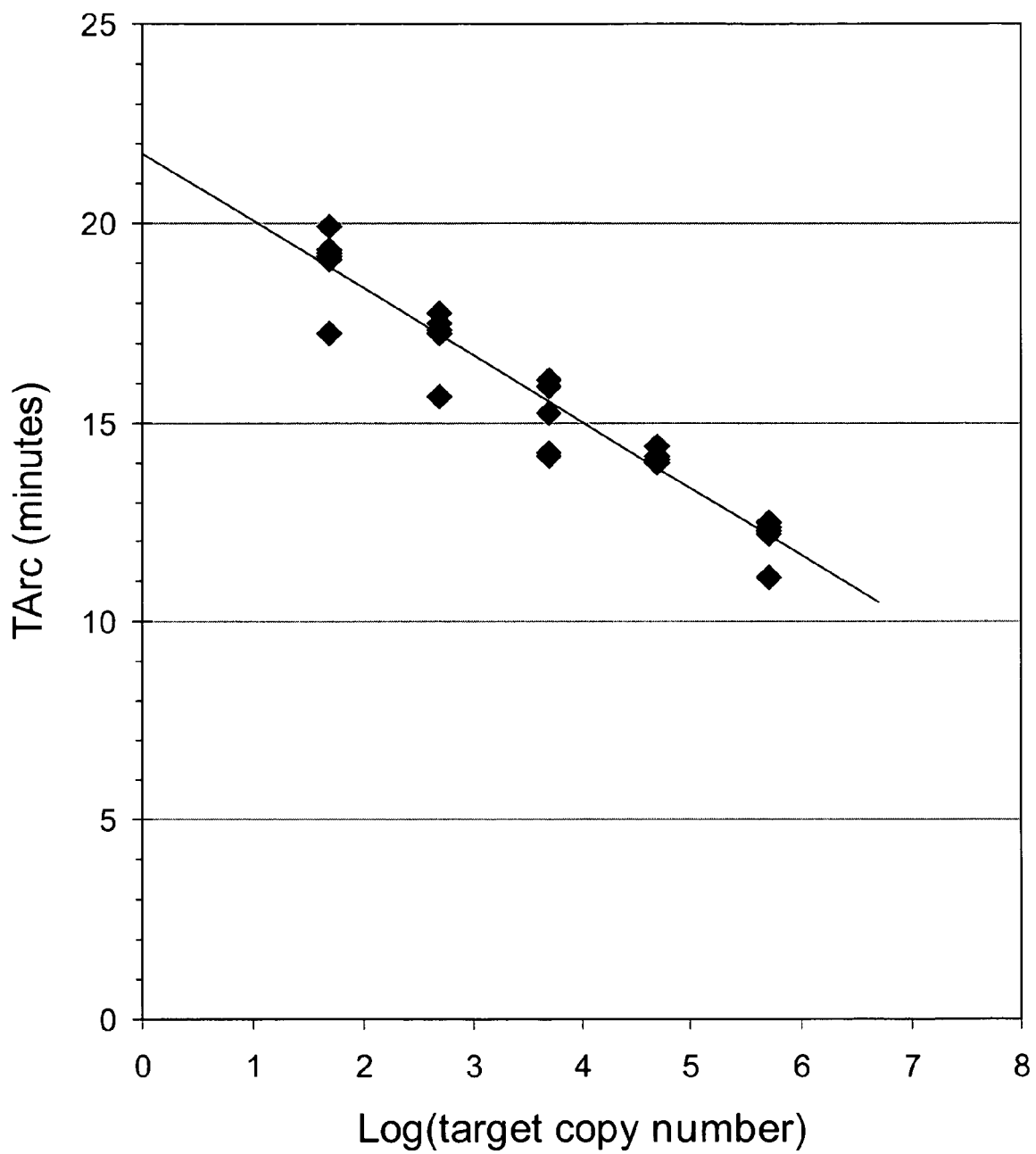
FIG. 12 is a graph showing results from a vector-based analysis of experimental data appearing in FIG. 7 after processing using a curve-fitting smoothing function (equation 5, below). The graph relates the amount of an HIV-1 analyte polynucleotide standard that was input into a real-time nucleic acid amplification reaction (x-axis) and the calculated TArc time (y-axis). Data points (filled diamonds) represent calculated TArc values for individual growth curves.

As indicated by the results presented in Table 8 and in FIG. 12, there was a strong relationship between the determined TArc values and the log of the input template copy number. Scatter among the data points plotted in FIG. 12 resulted from variation among the data plotted in the curves of FIG. 7. Clearly, the disclosed algorithm could be used to process experimental data that had been smoothed by a first curve-fitting approach to yield a relationship between the amount of template input into an amplification reaction and the determined TArc value. Parameters of the line determined using the TArc values appear in Table 9.

TABLE 9

Parameters of Lines Determined in FIGS. 8–12 Using the Vector-Based Algorithm

| Test Condition | Slope (min/log copy number) | Intercept (min) | R squared |
|---|---|---|---|
| Raw Data | −1.74 | 22.4 | 0.937 |
| Moving Average | −1.82 | 22.7 | 0.958 |
| Curve Fit (A) | −1.67 | 21.7 | 0.928 |
| Curve Fit (B) | −1.67 | 21.7 | 0.921 |
| Curve Fit (C) | −1.68 | 21.8 | 0.928 |

The results summarized in Table 9 indicated that all of the different analysis procedures yielded substantially identical results. Thus, the vector-based method was useful for analyzing raw experimental data, as well as data that had been processed by a smoothing function.

Example 2 describes how the vector-based algorithm employing directionally opposed vectors was used to analyze results from real-time nucleic acid amplification reactions. A comparative analysis carried out using the vector-based algorithm employing directionally similar vectors is also presented. As demonstrated by the results appearing below, both of the vector-based algorithms gave substantially equivalent results even though the curve features identified by the two approaches were different.

Example 2

Application of the Vector-Based Analytical Method Using Directionally Opposed Vectors A single set of results from time-dependent monitoring of nucleic acid amplification reactions were processed in parallel using a computer running a program to execute independent algorithms employing directionally similar vectors, or directionally opposed vectors. TMA reactions that amplified an HIV-1 analyte polynucleotides were carried out using analyte polynucleotide amounts that ranged from 0-5×10$^5$ copies/reaction. All reactions included a fluorescently labeled molecular torch hybridization probe specific for the HIV-1 amplicon. Fluorescence readings indicating the amounts of amplicon present in the reactions were recorded every 19.4 seconds, approximately. The numerical results from the amplification reactions were processed for smoothing by a four-point curve fit using the above-described Model A (equation (3)). Initial estimates for the different variables are given above in connection with the discussion of this mathematical model. A reiterative process of adjusting the values of the different variables was carried out to determine an optimized equation for each curve, also as described above. Thereafter, the growth curve represented by the determined equation was parsed into 5 second time units, and the vector analyses conducted using these time points as the origins for a series of vectors.

The algorithm employing directionally opposed vectors used a 50 second x-component magnitude to establish each member of a plurality of paired sets of vectors that incremented along the x-dimension of the processed growth curves. Thus, x-components of the vectors in this procedure incremented as described in Table 2. In accordance with this algorithm, the identified feature of each curve was the time value (i.e., a point on the x-axis) at which the angle between vectors among the collection of paired sets of directionally opposed vectors became minimal (i.e., the OTArc value). This is illustrated in FIG. 5B. A summary of these results appear in Table 10.

The algorithm employing directionally similar vectors used a 5 second x-component magnitude to establish the first member, and an 85 second x-component magnitude to establish the second member of a plurality of paired sets of vectors that incremented along the x-dimension of the processed growth curves. Thus, the x-components of the vectors in the procedure incremented as described in Table 1. In accordance with this algorithm, the identified feature of each curve was the time value (i.e., a point on the x-axis) at which the angle between vectors among the collection of paired sets of vectors became maximal (i.e., the TArc value). A summary of these results appear in Table 11.

TABLE 10

Summary of the Analysis Performed Using a Vector-Based Algorithm Employing Directionally Opposed Vectors

| Input Target Amt. (copy no.) | Avg. OTArc | Std. Dev. OTArc | Avg. Log Copy No. | Std. Dev. Log Copy No. |
|---|---|---|---|---|
| 0 | NA | NA | NA | NA |
| $1 \times 10^1$ | 14.0 | 2.83 | 0.72 | 2.02 |
| $5 \times 10^1$ | 12.6 | 0.98 | 1.71 | 0.70 |
| $5 \times 10^2$ | 11.0 | 0.18 | 2.89 | 0.13 |
| $5 \times 10^3$ | 9.8 | 0.16 | 3.72 | 0.11 |
| $5 \times 10^4$ | 8.4 | 0.12 | 4.70 | 0.09 |
| $5 \times 10^5$ | 7.2 | 0.11 | 5.62 | 0.08 |

NA: Not applicable

TABLE 11

Summary of the Analysis Performed Using a Vector-Based Algorithm Employing Directionally Similar Vectors

| Input Target Amt. (copy no.) | Avg. TArc | Std. Dev. TArc | Avg. Log Copy No. | Std. Dev. Log Copy No. |
|---|---|---|---|---|
| 0 | NA | NA | NA | NA |
| $1 \times 10^1$ | 13.5 | 2.81 | 0.72 | 2.02 |
| $5 \times 10^1$ | 12.1 | 0.99 | 1.71 | 0.71 |
| $5 \times 10^2$ | 10.5 | 0.19 | 2.90 | 0.14 |
| $5 \times 10^3$ | 9.3 | 0.13 | 3.72 | 0.09 |
| $5 \times 10^4$ | 8.0 | 0.11 | 4.70 | 0.08 |
| $5 \times 10^5$ | 6.7 | 0.10 | 5.61 | 0.07 |

NA: Not applicable

Comparison of the results presented in Table 10 and Table 11 confirmed that the two vector-based algorithms yielded virtually identical results, except that the average values for TArc and OTArc were shifted in time by about 0.5 minutes, as expected. Clearly, the two algorithms provided extraordinarily consistent results, and can be used for analyzing the results from real-time nucleic acid amplification reactions. More particularly, either algorithm can be used to establish a standard curve, or determine the amount or concentration of an analyte polynucleotide in a test sample. Moreover, either algorithm can be used to analyze raw experimental data representing a growth curve, or to analyze experimental data after processing using a smoothing operation. Exemplary smoothing operations include smoothing by calculating moving averages, and smoothing by curve-fitting to establish an optimized equation which can be solved for arbitrarily parsed time increments.

The foregoing description proves that any vector-based algorithm which identifies a consistent feature of a growth curve can be used for analyzing results from real-time nucleic acid amplification reactions to yield standard plots or to quantify analyte polynucleotides in a test sample. Useful algorithms can employ paired sets of directionally similar vectors, or paired sets of directionally opposed vectors. The different members of a single set of vectors can have identical or different magnitudes in a dimension employed for incrementing sets of vectors along the growth curve undergoing analysis. Moreover, useful vector-based algorithms can be used to analyze raw experimental results, or results processed by a smoothing function. Examples of preferred smoothing functions include calculation of moving averages, and curve-fitting operations.

This invention has been described with reference to a number of specific examples and embodiments thereof. Of course, a number of different embodiments of the present invention will suggest themselves to those having ordinary skill in the art upon review of the foregoing detailed description. Thus, the true scope of the present invention is to be determined upon reference to the appended claims.

What is claimed is:

1. A method for determining the amount of a nucleic acid in a test sample, comprising the steps of:

amplifying a predetermined locus of the nucleic acid in an in vitro amplification reaction to create a nucleic acid amplification product;

determining a value proportional to the amount of the nucleic acid amplification product present at different times during the in vitro amplification reaction, whereby there is created a collection of time-dependent values that collectively define a growth curve;

performing a vector analysis on at least a portion of said growth curve to identify a time-dependent feature indicating a transition from the baseline phase into the growth phase of said growth curve, said vector analysis comprising the steps of, (a) establishing a plurality of pairs of first and second vectors at different points on a time dimension of the growth curve using said collection of time-dependent values, wherein each vector of a single pair of vectors among said plurality has the same origin, and wherein the head of the first vector and the head of the second vector of said single pair of vectors among said plurality are each positioned at different points on the growth curve, (b) calculating for each pair of vectors the value of an angle therebetween, thereby resulting in a plurality of calculated angles, with each point on the time dimension of the growth curve being associated with a different one of said plurality of calculated angles, (c) comparing the plurality of calculated angles with each other to identify a characteristic angle, and (d) identifying said time-dependent feature of said growth curve as the point on the time dimension of the growth curve that is associated with the characteristic angle, said characteristic angle being either the maximum angle among the plurality of calculated angles or the minimum angle among the plurality of calculated angles;

comparing the time-dependent feature identified in step (d) with a standard calibration curve; and determining from said time-dependent feature of said growth curve and said standard calibration curve the amount of the nucleic acid in the test sample.

2. The method of claim 1, wherein said characteristic angle is the minimum angle among the plurality of calculated angles.

3. The method of claim 1, wherein said characteristic angle is the maximum angle among the plurality of calculated angles.

4. The method of claim 1, wherein each vector in said single pair of vectors has a different magnitude in said time dimension of said growth curve, said vectors being directionally similar vectors, and wherein said characteristic angle is the maximum angle among the plurality of calculated angles.

5. The method of claim 1, wherein each vector in said single pair of vectors has a different magnitude in said time dimension of said growth curve, said vectors being directionally opposed vectors, and wherein said characteristic angle is the minimum angle among the plurality of calculated angles.

6. The method of claim 1, wherein each vector in said single pair of vectors has the same magnitude in said time dimension of said growth curve, said vectors being directionally opposed vectors, and wherein said characteristic angle is the minimum angle among the plurality of calculated angles.

7. The method of claim 1, further comprising a processing step before the step for performing the vector analysis, said processing step comprising processing said collection of time-dependent values of the first determining step by a smoothing function to result in smoothed numerical data, and wherein the collection of time-dependent values used in step (a) of the vector analysis is the smoothed numerical data resulting from the processing step.

8. The method of claim 7, wherein the smoothing function in the processing step is selected from the group consisting of a moving average smoothing function, and a curve-fitting smoothing function.

9. The method of claim 7, wherein each vector in said single pair of vectors has a different magnitude in said time dimension of said growth curve, said vectors being directionally similar vectors, and wherein said characteristic angle is the maximum angle among the plurality of calculated angles.

10. The method of claim 7, wherein each vector in said single pair of vectors has a different magnitude in said time dimension of said growth curve, said vectors being directionally opposed vectors, and wherein said characteristic angle is the minimum angle among the plurality of calculated angles.

11. The method of claim 7, wherein each vector in said single pair of vectors has the same magnitude in said time dimension of said growth curve, said vectors being directionally opposed vectors, and wherein said characteristic angle is the minimum angle among the plurality of calculated angles.

12. The method of claim 1, wherein said in vitro amplification reaction in the amplifying step is an isothermal in vitro amplification reaction.

13. The method of claim 12, wherein the value proportional to the amount of the nucleic acid amplification product in the first determining step is a fluorescence value.

14. The method of claim 1, wherein the step for performing the vector analysis is automated by a computer.

15. The method of claim 1, wherein the determined amount of said nucleic acid in the test sample is recorded in tangible form.

16. The method of claim 1, wherein the steps for performing a vector analysis, comparing the time dependent feature, and determining from said time-dependent feature, are automated by a computer.

* * * * *